United States Patent
Baker et al.

(10) Patent No.: US 12,004,865 B2
(45) Date of Patent: Jun. 11, 2024

(54) SEPSIS DETECTION AND MONITORING

(71) Applicant: Welch Allyn, Inc., Skaneateles Falls, NY (US)

(72) Inventors: Steven D. Baker, Beaverton, OR (US); Jotpreet Chahal, Fayetteville, NY (US); Stacey Fitzgibbons, Dewitt, NY (US); Craig M. Meyerson, Syracuse, NY (US); David E. Quinn, Auburn, NY (US); Lori Ann Zapfe, Milroy, IN (US); Gene J. Wolfe, Pittsford, NY (US)

(73) Assignee: Welch Allyn, Inc., Skaneateles Falls, NY (US)

( * ) Notice: Subject to any disclaimer, the term of this patent is extended or adjusted under 35 U.S.C. 154(b) by 0 days.

(21) Appl. No.: 18/339,389

(22) Filed: Jun. 22, 2023

(65) Prior Publication Data
US 2023/0329628 A1    Oct. 19, 2023

Related U.S. Application Data

(63) Continuation of application No. 16/832,672, filed on Mar. 27, 2020, now Pat. No. 11,730,421.
(Continued)

(51) Int. Cl.
  *A61B 5/00*    (2006.01)
  *A61B 5/1455*  (2006.01)
  *A61B 5/1491*  (2006.01)

(52) U.S. Cl.
  CPC .......... *A61B 5/412* (2013.01); *A61B 5/14552* (2013.01); *A61B 5/1491* (2013.01); *A61B 5/6831* (2013.01); *A61B 5/742* (2013.01)

(58) Field of Classification Search
  CPC ... A61B 5/412; A61B 5/14552; A61B 5/1491; A61B 5/6831; A61B 5/742;
  (Continued)

(56) References Cited

U.S. PATENT DOCUMENTS 5,158,082 A    10/1992   Jones
6,155,976 A *  12/2000   Sackner ............... A61H 31/008
                                                    600/300
(Continued)

FOREIGN PATENT DOCUMENTS

EP    0 247 777 A1     2/1987
JP    2015-188580 A   11/2015
(Continued)

OTHER PUBLICATIONS

Extended European Search Report for Application No. 20166493.5, dated Aug. 31, 2020.
(Continued)

*Primary Examiner* — Eric F Winakur
*Assistant Examiner* — Abid A Mustansir
(74) *Attorney, Agent, or Firm* — Merchant & Gould P.C.

(57) ABSTRACT

A sensor device includes a housing defining a cavity, an inlet to receive fluid pumped from an instrument device, an outlet to return the fluid to a fluid reservoir, and a fluid channel defined inside the cavity between the inlet and the outlet. A heat pump is mounted inside the cavity, and has a side surface thermally coupled to the fluid channel and an opposite side surface thermally coupled to a plate. The heat pump is configured to induce a temperature change. A sensor unit is aligned with an aperture in the plate and includes an optical component and a thermal component. The optical component configured to measure a vascular endothelial response from the induced temperature change.

20 Claims, 21 Drawing Sheets

Related U.S. Application Data

(60) Provisional application No. 62/825,844, filed on Mar. 29, 2019.

(58) Field of Classification Search
CPC ..... A61B 3/0025; A61B 3/12; A61B 5/02007; A61B 5/0531; A61B 5/0048; A61B 5/14558

See application file for complete search history.

(56) References Cited

U.S. PATENT DOCUMENTS

| | | | |
|---|---|---|---|
| 6,248,066 | B1 | 6/2001 | Barnett et al. |
| 8,064,976 | B2 | 11/2011 | Ince |
| 8,243,999 | B2 | 8/2012 | Tobin, Jr. et al. |
| 8,805,051 | B2 | 8/2014 | Najarian et al. |
| 8,914,089 | B2 | 12/2014 | Abreu |
| 9,053,222 | B2 | 6/2015 | Lynn et al. |
| 9,131,861 | B2 | 9/2015 | Ince et al. |
| 9,498,138 | B2 | 11/2016 | Zuckerman-Stark et al. |
| 9,943,240 | B2 | 4/2018 | Vallee et al. |
| 2004/0064057 | A1 | 4/2004 | Siegel |
| 2004/0132171 | A1 | 7/2004 | Rule et al. |
| 2004/0249265 | A1 | 12/2004 | Fuchs et al. |
| 2007/0173735 | A1 | 7/2007 | Callister et al. |
| 2008/0091088 | A1* | 4/2008 | Kiani ............. A61B 5/0205 600/301 |
| 2013/0030259 | A1 | 1/2013 | Thomsen et al. |
| 2014/0018649 | A1 | 1/2014 | Jespersen et al. |
| 2016/0367173 | A1 | 12/2016 | Dalvi et al. |
| 2017/0367574 | A1 | 12/2017 | Belthangady et al. |
| 2018/0020964 | A1 | 1/2018 | Newberry |
| 2018/0303352 | A1 | 10/2018 | Feng et al. |
| 2018/0360307 | A1 | 12/2018 | Oh et al. |
| 2018/0360386 | A1 | 12/2018 | LeBoeuf et al. |
| 2020/0275877 | A1* | 9/2020 | Fitzgibbons ............ A61B 5/024 |

FOREIGN PATENT DOCUMENTS

| | | |
|---|---|---|
| KR | 20150095346 A | 8/2015 |
| WO | 2017062484 A1 | 4/2017 |
| WO | 2019027895 A1 | 2/2019 |

OTHER PUBLICATIONS

Gyang, E et al. "A Nurse-Driven Screening Tool for the Early Identification of Sepsis in an Intermediate Care Unit Setting." J Hosp Med. (Feb. 2015); 10(2): 97-103.

Jones AE, et al. "Use of Goal-Directed Therapy for Severe Sepsis and Septic Shock in Academic Emergency Departments." Crit Care Med. (2005);33(8):1888-1889; author reply 1889-1890.

Orbegozo, D. et al. "Skin microcirculatory reactivity assessed using a thermal challenge is decreased in patients with circulatory shock and associated with outcome." Annals of Intensive Care 8:60 (2018), 1-9.

Poplin, R., et al., "Prediction of cardiovascular risk factors from retinal fundus phtographs via deep learning." Nature Biomedical Engineering (2018), pp. 1-9.

Stoneking, L. et al. "Sepsis Bundles and Compliance with Clinical Guidelines." Journal of Intensive Care Medicine, (2011), 26(3), 172-182.

* cited by examiner

SEPSIS DETECTION AND MONITORING

INTRODUCTION

Sepsis is a life-threatening condition that occurs when the body's response to infection causes injury to its own tissues and organs. Sepsis develops when a pathogen is released into the bloodstream and causes inflammation throughout the entire body.

In early stages, it is difficult to differentiate sepsis from other diseases because certain symptoms of sepsis, such as fever, increased heart rate, and breathing rate, mimic the symptoms of other diseases. The ability to detect sepsis at its earliest stages is critical because early sepsis is usually reversible with antibiotics, fluids, and other supportive medical interventions. However, as time progresses the risk of dying increases substantially.

The costs of enrolling a non-septic patient include unnecessary hospital admission, antibiotics, blood draws, and blood cultures, and failure to address the patient's actual clinical need. The costs of a false negative include, at worst, patient death and, at best, longer length of stay at a higher acuity ward such as an ICU. The combination of the high mortality rate of sepsis and the difficulty differentiating it from other diseases leads to current systems for sepsis detection to be biased toward false positives.

SUMMARY

In general terms, the present disclosure relates to non-invasive screening for sepsis. Additionally, while the following methods, systems, and devices are described as directed to detecting and monitoring for sepsis, it is contemplated that these methods, systems, and devices can be used to detect and monitor additional types of microvascular disease states.

In one aspect, a sensor device comprises: a housing defining a cavity, an inlet to receive fluid pumped from an instrument device, an outlet to return the fluid to a fluid reservoir, and a fluid channel defined inside the cavity between the inlet and the outlet; a heat pump mounted inside the cavity, the heat pump having a side surface thermally coupled to the fluid channel, and an opposite side surface thermally coupled to a plate, the heat pump configured to induce a temperature change; and a sensor unit aligned with an aperture in the plate, the sensor unit including an optical component and a thermal component, the optical component configured to measure a vascular endothelial response from the induced temperature change.

The heat pump can be mounted over the fluid channel to seal the fluid inside the fluid channel between the inlet and the outlet. The fluid channel can be shaped to have a serpentine configuration to increase a surface area contact between the fluid and the heat pump. In one embodiment, the heat pump is a Peltier device. The housing includes one or more tabs positioned on an exterior of the housing, the tabs being structured to receive a strap or band. The housing can include a structure defining a loop that is structured to fix the conduit relative to the housing. The heat pump can cool the plate to induce a temperature of about 18° C. on a skin surface. The heat pump can heat the plate to induce a temperature of about 40° C. on a skin surface. In one embodiment, the optical component is a photoplethysmogram sensor that measures photoplethysmogram data at the induced temperature change. In one embodiment, the thermal component measures skin surface temperatures to provide a closed loop feedback control.

In another aspect, a system for non-invasive screening of sepsis, comprises: an instrument device, the instrument device including: a pump to pump fluid from a fluid reservoir through a coolant loop; and a power supply; a sensor device, the sensor device including: a housing defining a cavity, an inlet to receive the fluid pumped from the instrument device, an outlet to return the fluid to the fluid reservoir, and a fluid channel defined inside the cavity between the inlet and the outlet; a heat pump mounted inside the cavity, the heat pump having a side surface thermally coupled to the fluid channel, and an opposite side surface thermally coupled to a plate, the heat pump configured to induce a temperature change; and a sensor unit mounted to a flexible cable that conforms to the shape of the housing, the sensor unit aligned with an aperture in the plate, the sensor unit including an optical component and a thermal component, the optical component being configured to measure a vascular endothelial response from the induced temperature change; and a conduit connecting the sensor device to the instrument device, the conduit including an inlet tube to supply the fluid from the fluid reservoir to the inlet of the sensor device, an outlet tube to transfer the fluid from the outlet of the sensor device to the fluid reservoir, and one or more cables to supply control voltages from the power supply in the instrument device to the heat pump of the sensor device.

The instrument device can include a radiator and fan to cool the fluid held in the fluid reservoir. The instrument device can further have a voltage regulator to regulate the supply of the control voltages from the instrument device to the heat pump. The instrument device can be connectable to a display screen to display the vascular endothelial response measured by the sensor unit. The heat pump can cool the plate to induce a temperature of about 18° C. on a skin surface and can heat the plate to induce a temperature of about 40° C. on the same skin surface.

In another aspect, a sensor device comprises: a heat pump configured to induce a temperature change on a skin surface; and an optical component, the optical component having: a light emitter configured to transmit optical signals that penetrate the skin surface to reach a blood vessel; a first polarizer mounted over the light emitter, the first polarizer polarizing the light signals from the light emitter in a polarized direction; a light detector configured to receive optical signals reflected back from the blood vessel, the reflected optical signals being used to measure a vascular endothelial response from the induced temperature change; and a second polarizer mounted over the light detector, the second polarizer arranged out of phase with respect to the first polarizer to filter the reflected optical signals received by the light detector, wherein the first and second polarizers are independently adjustable such that the angles of incidence of each of the first and second polarizers are adjustable.

The sensor device can comprise an optical block housed in the body, the optical block configured to prevent the light signals transmitted from the light emitter from passing directly to the light detector without first being reflected back from the blood vessel. The second polarizer filters the reflected optical signals such that only the optical signals that reflect off a blood vessel are received by the light detector, while the optical signals that do not reach the blood vessel are blocked. The orientation of the first and second polarizers can be adjustable to align with an orientation of a blood vessel to maximize the strength of the optical signals reflected back from the blood vessel regardless of a position of the sensor device. The angles of incidence of the first and second polarizers are modulated based on the induced temperature change.

In another aspect, a system for non-invasive screening of sepsis comprises: a processor and a memory, wherein the memory stores instructions that, when executed by the processor, cause the system to: receive fundus images; compare the fundus images to stored fundus images of patients previously identified as non-septic and in various stages of septic progression; and provide an estimate of sepsis progression level.

In another aspect, a system for non-invasive screening of sepsis comprises: a temperature induction device; a sensor coupled to the temperature induction device; and a processor and a memory; wherein the memory stores instructions that, when executed by the processor, cause the system to: apply a first induced temperature pulse; collect a first set of data after the first induced temperature pulse; apply a second induced temperature pulse; collect a second set of data after the second induced temperature pulse; and compare the first and second sets of data to screen for sepsis.

In a further aspect, a system for evaluating sepsis treatment comprises: a patient support device including a frame connected to a motor, the frame configured to tilt at an angle relative to the ground; a medical device configured to measure one or more vital signs before and after the frame is tilted; and a control device having a processor and a memory, wherein the memory stores instructions that, when executed by the processor, cause the system to: receive a first vital sign measurement when the surface is in a rested position; receive a second vital sign measurement when the surface is in a tilted positon; and compare the first and second vital sign measurements to determine whether a status of a septic patient is improving.

DESCRIPTION OF THE FIGURES

The following drawing figures, which form a part of this application, are illustrative of the described technology and are not meant to limit the scope of the disclosure in any manner.

DETAILED DESCRIPTION

Figure 1:
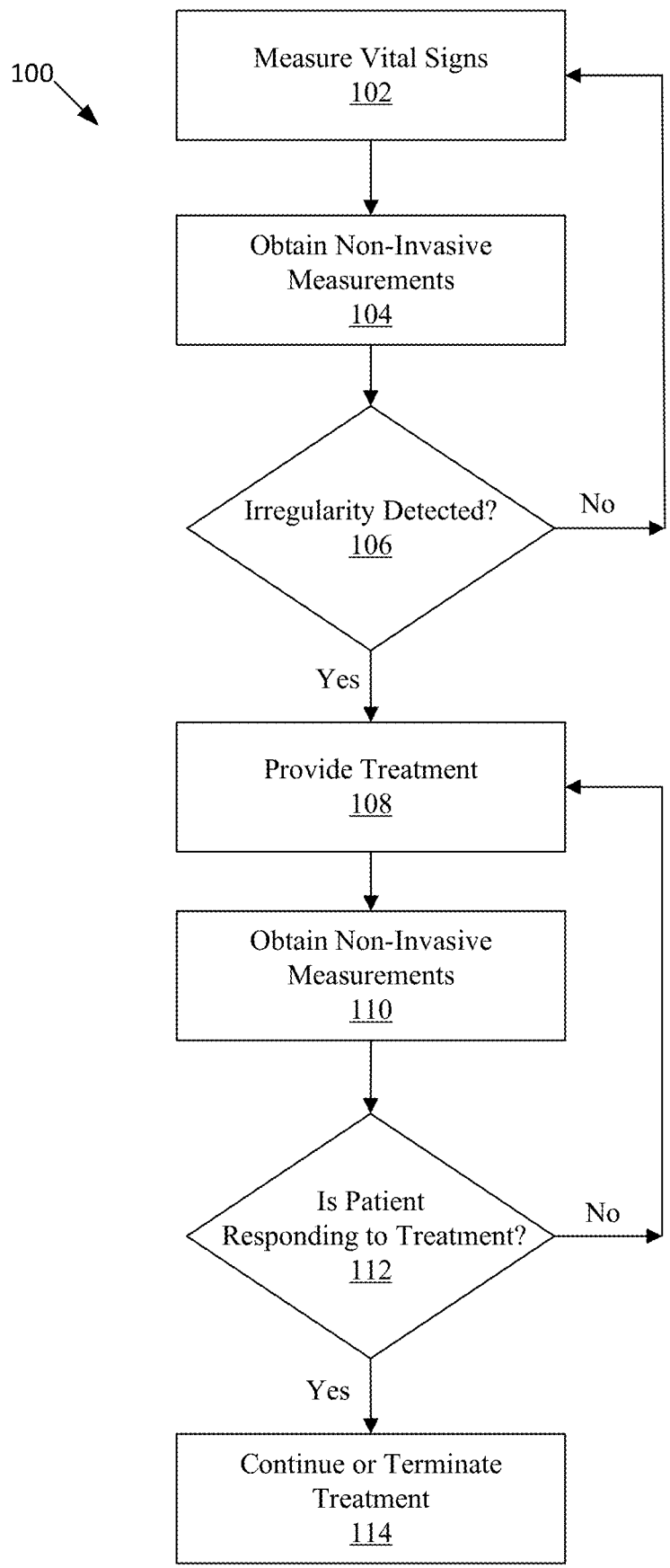
FIG. 1 schematically illustrates a method of detecting and monitoring sepsis.

FIG. 1 illustrates a method 100 of detecting and monitoring sepsis. The method 100 includes measuring vital signs (Step 102); obtaining non-invasive measurements (Step 104); determining if an irregularity is detected (Step 106); providing treatment (Step 108); obtaining additional non-invasive measurements during treatment (Step 110); determining whether a septic patient is responding to treatment (Step 112); and continuing or terminating treatment (Step 114).

Referring now to Step 102, vital sign measurements are obtained from a vital signs monitor such as a Connex® spot monitor available from Welch Allyn Inc., Skaneateles Falls, NY. In one example embodiment, heart rate variability is measured in Step 102 because heart rate variability has been shown to decrease before the clinical onset of sepsis. Heart rate variability is a measure of the variation in time between each heartbeat. If a decrease in heart rate variability is detected, the rate of acquiring the vital signs in Step 102 is increased.

The heart rate variability can be measured via electrocardiography (ECG). Alternatively, the heart rate variability can be measured via a photoplethysmogram (PPG). In a further example, the heart rate variability can be measured via a radar signal transmission from a monitoring device similar to the device described in U.S. Provisional Patent Application No. 62/798,124 filed on Jan. 29, 2019, the entirety of which is hereby incorporated by reference.

Referring now to Step 104, non-invasive measurements are obtained to screen for sepsis. In accordance with the description that follows, non-invasive measurements are measurements beyond basic vital signs.

In a first example embodiment, skin surface temperatures are measured to screen for sepsis. Capillary flow is consistent in non-septic patients, but has higher variation as sepsis progresses. Thus, septic patients have higher variation in skin surface temperatures than non-septic patients due to capillary flow irregularities. In this example embodiment, skin surface temperatures are recorded and compared to values previously recorded for the same patient or to values from other patients to screen patients for sepsis.

A skin surface temperature irregularity is determined when one portion of the body has a different temperature than another portion of the body. The skin surface temperature irregularity can indicate that the body is dysregulated such that the blood capillaries in the body are experiencing different distribution rates of blood. The locations where skin surface temperature irregularities are detected can provide guide points for further analysis such as for measuring microvascular response in the detected location.

In some instances, a variation in skin surface temperature is normal due to portions of the body being exposed to ambient air while other portions are covered. For example, the skin surface temperatures on the extremities of the body (e.g., hands, feet, head, etc.) are often different from the skin surface temperatures on other portions of the body (e.g., chest, abdomen, etc.). Thus, these variations are taken into consideration when determining where skin surface temperature irregularities are present on the body of a patient undergoing sepsis screening.

For example, the skin surface temperatures of a patient's body can be monitored over time, and changes in the skin surface temperatures can be compared to values previously recorded for the patient to determine whether an irregularity exists. Alternatively, changes in the skin surface temperatures can be compared to values from other patients to determine whether an irregularity exists. Algorithms can be used to determine whether the changes in skin surface temperature indicate that the body is dysregulated to screen a patient for sepsis.

In one example embodiment, peripheral temperature gradients such as fingertip to forearm temperature ratio are measured. This ratio can indicate perfusion abnormalities.

In another example embodiment, detection and monitoring of skin mottling is performed. For example, skin mottling can be tracked at or below the knee as an indicator of perfusion abnormalities, and hence as an indicator of whether a patient is septic.

In one example embodiment, the skin surface temperature is measured using a thermal imager. The thermal imager is a heat camera that is retrofitted from measuring core body temperature to measuring skin surface temperature. The thermal images acquired from the thermal imager can be trended to monitor for irregularities in skin surface temperature.

As shown in FIG. 1, if irregularities in skin surface temperature are not detected (Step 106), the method 100 returns to measuring vital signs (Step 102). If irregularities in skin surface temperature are detected (Step 106), the patient is screened as having sepsis and the method 100 proceeds to provide sepsis treatment (Step 108).

In another example embodiment, non-invasive measurements are obtained to screen for sepsis in Step 104 by capturing fundus images of the eye to screen for sepsis. In this example embodiment, the fundus images are captured by a fundus imaging system. In one example, the fundus imaging system is similar to the system described in U.S. patent application Ser. No. 15/054,558 filed on Feb. 26, 2016, the entirety of which is hereby incorporated by reference. In another example, the fundus imaging system is similar to the system described in U.S. Provisional Patent Application No. 62/783,689 filed on Dec. 21, 2018, the entirety of which is hereby incorporated by reference.

Figure 2:
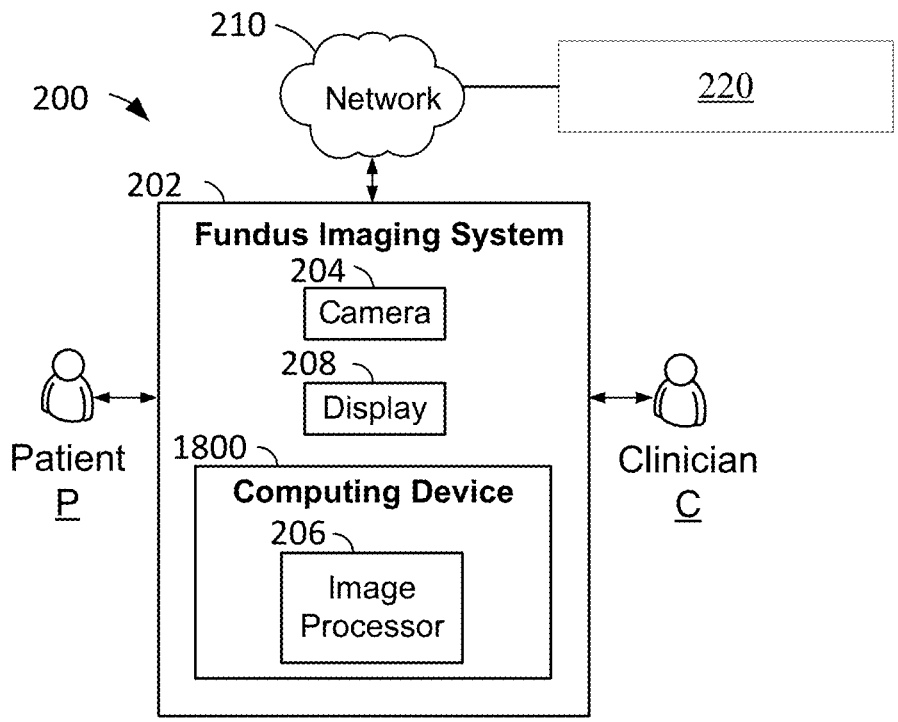
FIG. 2 is a schematic block diagram illustrating an example system for recording and viewing an image of a patient's fundus.

FIG. 2 is a schematic block diagram illustrating an example system 200 for capturing fundus images. The system 200 includes a patient P, a fundus imaging system 202, and a computing device 1800 that includes an image processor 206. A camera 204 and display 208 are in communication with the computing device 1800. The system 200 further includes a network 210 that connects the fundus imaging system 202 to an analysis engine 220. In an alternative example, the analysis engine 220 is a component within the computing device 1800.

The fundus imaging system 202 functions to create a set of digital images of a patient's P eye fundus. As used herein, "fundus" refers to the eye fundus and includes the retina, optic nerve, macula, vitreous, choroid and posterior pole. In this example, the fundus imaging system 202 is configured to capture a set of fundus images over a time duration that covers a complete cardiac cycle such that the fundus images are captured during both systole and diastole portions of the cardiac cycle. The systole portion occurs when the chambers of the heart muscle contract after refilling with blood, while the diastole portion occurs when the heart refills with blood after the emptying done during the systole portion of the cardiac cycle. Thus, a series of images are captured to view the fundus of the eye during a complete cardiac cycle. In one illustrative example, the series of images are captured at a rate of 10 frames per second.

The fundus imaging system 202 includes a handheld housing that supports the system's components. The housing supports one or two apertures for imaging one or two eyes at a time. In embodiments, the housing supports positional guides for the patient P, such as an optional adjustable chin rest. The positional guide or guides help to align the patient's P eye or eyes with the one or two apertures. In embodiments, the housing supports means for raising and lowering the one or more apertures to align them with the patient's P eye or eyes. Once the patient's P eyes are aligned, the clinician C then initiates the image captures.

One technique for fundus imaging requires mydriasis, or the dilation of the patient's pupil, which can be painful and/or inconvenient to the patient P. Example system 200 does not require a mydriatic drug to be administered to the patient P before imaging, although the system 200 can image the fundus if a mydriatic drug has been administered.

The system 200 can be used to assist the clinician C in screening for, monitoring, or diagnosing sepsis in addition to various eye diseases, such as hypertension, diabetic retinopathy, glaucoma and papilledema. It will be appreciated that the clinician C that operates the fundus imaging system 202 can be different from the clinician C evaluating the resulting image.

The fundus imaging system 202 includes a camera 204 in communication with an image processor 206. In this embodiment, the camera 204 is a digital camera including a lens, an aperture, and a sensor array. The camera 204 lens is a variable focus lens. The camera 204 is configured to record images of the fundus one eye at a time. In other examples, the camera 204 is configured to record an image of both eyes substantially simultaneously. In those embodiments, the fundus imaging system 202 can include two separate cameras, one for each eye.

In example system 200, the image processor 206 is operatively coupled to the camera 204 and configured to communicate with the network 210 and display 208. The image processor 206 regulates the operation of the camera 204. Components of an example computing device 1800 are described in more detail with reference to FIG. 22.

The display 208 is in communication with the image processor 206. In one example, the housing supports the display 208. In another example, the display 208 is part of an external smart phone, tablet computer, or monitor. The display 208 reproduces the images produced by the fundus imaging system 202 in a size and format readable by the clinician C. For example, the display 208 can be a liquid crystal display (LCD) and active matrix organic light emitting diode (AMOLED) display. The display 208 can be touch sensitive.

The fundus imaging system 202 is connected to a network 210. The network 210 may include any type of wireless network, a wired network, or any communication network known in the art. For example, wireless connections can include cellular network connections and connections made using protocols such as 802.11a, b, and/or g. In other examples, a wireless connection can be accomplished directly between the fundus imaging system 202 and an external display using one or more wired or wireless protocols, such as Bluetooth, Wi-Fi Direct, radio-frequency identification (RFID), or Zigbee. Other configurations are possible.

In the example depicted in FIG. 2, the fundus imaging system 202 is operable to communicate with the analysis engine 220 via the network 210. For example, the fundus imaging system 202 is configured to transmit the captured fundus images to the analysis engine 220 for further analysis via the network 210. In an alternative example, the analysis engine 220 is located in the computing device 1800 of the fundus imaging system 202.

Figure 3:
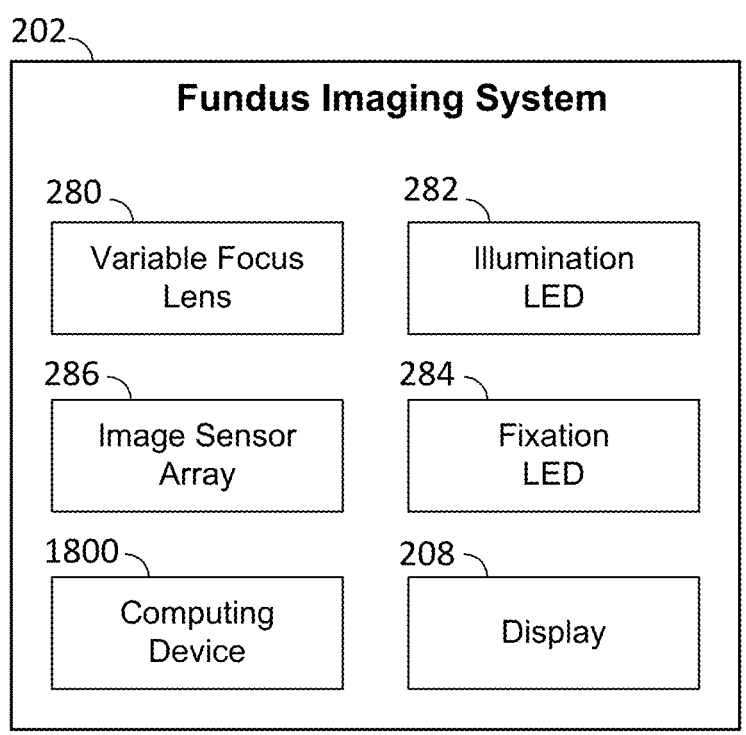
FIG. 3 illustrates components of an example fundus imaging system.

FIG. 3 illustrates the components of the fundus imaging system 202. As shown in FIG. 3, the fundus imaging system 202 includes a variable focus lens 280, an illumination LED 282, an image sensor array 286, a fixation LED 284, a computing device 1800, and a display 208. Each component is in electrical communication with, at least, the computing device 1800. Other example embodiments can include more or fewer components.

In one example, the variable focus lens 280 is a liquid lens. A liquid lens is an optical lens whose focal length can be controlled by the application of an external force, such as a voltage. The lens includes a transparent fluid, such as water or water and oil, sealed within a cell and a transparent membrane. By applying a force to the fluid, the curvature of the fluid changes, thereby changing the focal length. This effect is known as electrowetting.

In another example, the variable focus lens 280 is one or more movable lenses that are controlled by a stepping motor, a voice coil, an ultrasonic motor, or a piezoelectric actuator. Additionally, a stepping motor can also move the image sensor array 286. In those embodiments, the variable focus lens 280 and/or the image sensor array 286 are oriented normal to an optical axis of the fundus imaging system 202 and move along the optical axis.

The illumination LED 282 can be single color or multicolor. Optionally, the illumination LED 282 is an assembly including one or more visible light LEDs and a near-infrared LED. The optional near-infrared LED can be used in a preview mode, for example, for the clinician C to determine or estimate the patient's P eye focus without illuminating visible light that could cause the pupil to contract or irritate the patient P.

The illumination LED 282 is in electrical communication with the computing device 1800. Thus, the illumination of illumination LED 282 is coordinated with the adjustment of the variable focus lens 280 and image capture. The illumination LED 282 can be overdriven to draw more than the maximum standard current draw rating.

The fixation LED 284 produces a light to guide the patient's P eye for alignment. The fixation LED 284 can be a single color or multicolor light that appears as a dot when the patient P looks into the fundus imaging system 202.

The image sensor array 286 receives and processes light reflected by the patient's fundus. The image sensor array 286 is, for example, a complementary metal-oxide semiconductor (CMOS) sensor array, also known as an active pixel sensor (APS), or a charge coupled device (CCD) sensor. The image sensor array 286 has a plurality of rows and columns of pixels. The image sensor array can have about 1280 by 1024 pixels, about 640 by 480 pixels, about 1500 by 1152 pixels, about 2048 by 1536 pixels, or about 2560 by 1920 pixels. The pixel size in the image sensor array 286 can be from about four micrometers by about four micrometers; from about two micrometers by about two micrometers; from about six micrometers by about six micrometers; or from about one micrometer by about one micrometer.

The example image sensor array 286 includes photodiodes that have a light-receiving surface and have substantially uniform length and width. During exposure, the photodiodes convert the incident light to a charge. The image sensor array 286 can be operated as a global reset, that is, substantially all of the photodiodes are exposed simultaneously and for substantially identical lengths of time.

Referring now to FIG. 2, the analysis engine 220 compares the fundus images captured by the fundus imaging system 202 to stored fundus images of patients previously identified as non-septic and in various stages of septic progression. The analysis engine 220 uses a deep learning algorithm to determine whether there is microvascular dysregulation by looking for irregularities in the blood vessels in the patient P's eye. The deep learning apparatus may also use additional factors such as current diagnosis, medical history, and other ethnographic data. The analysis engine 220 screens the patient P for sepsis by using the deep learning algorithm to determine whether there is an indication of fundus microvascular dysregulation.

Figure 4:
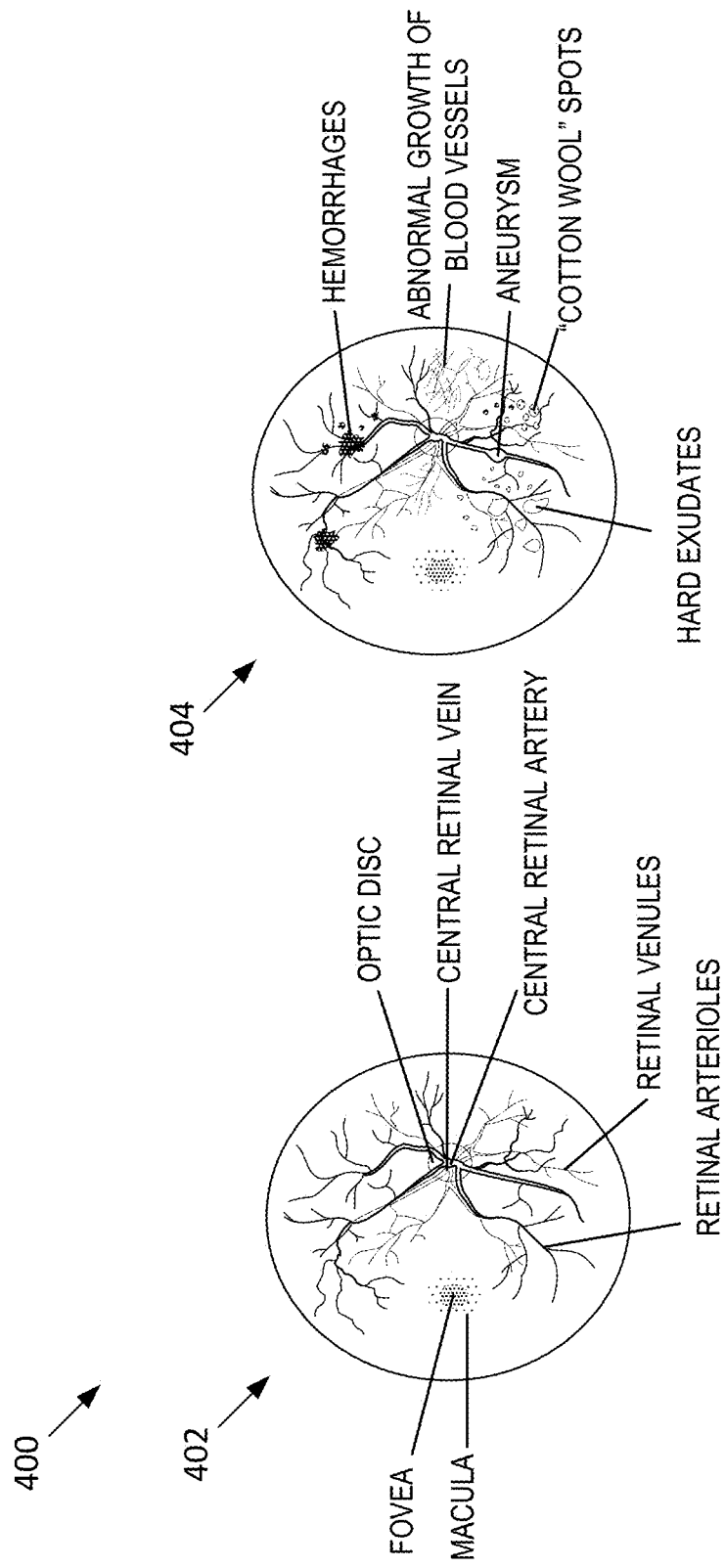
FIG. 4 illustrates a comparison between a normal fundus and a fundus displaying symptoms of microvascular dysregulation.

FIG. 4 illustrates a comparison 400 between a normal fundus 402 and a fundus 404 displaying symptoms of microvascular dysregulation. Signs of microvascular dysregulation include micro-hemorrhages, aneurysms (e.g., vascular beading), areas of decreased perfusion (e.g., "cotton wool spots"), macular edema, and abnormal vessels such as dilated arterioles.

Figure 5:
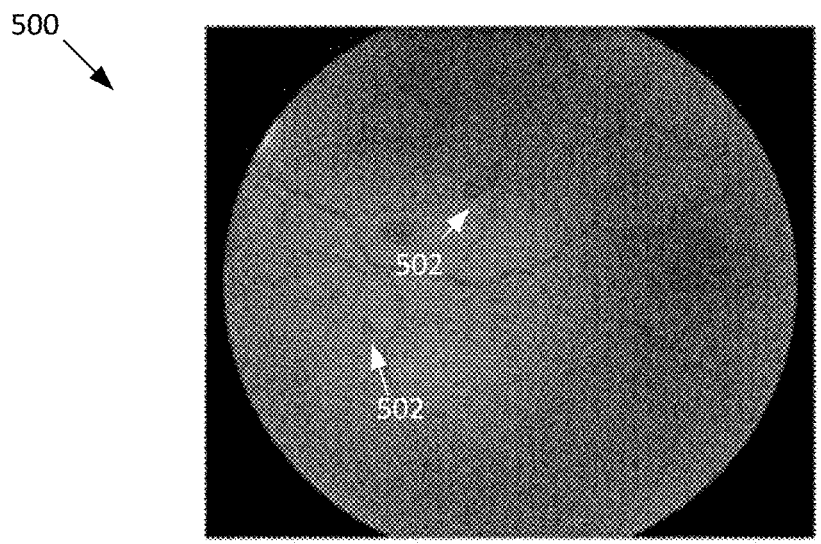
FIG. 5 is a detailed image of a fundus that includes micro-hemorrhages.
Figure 6:
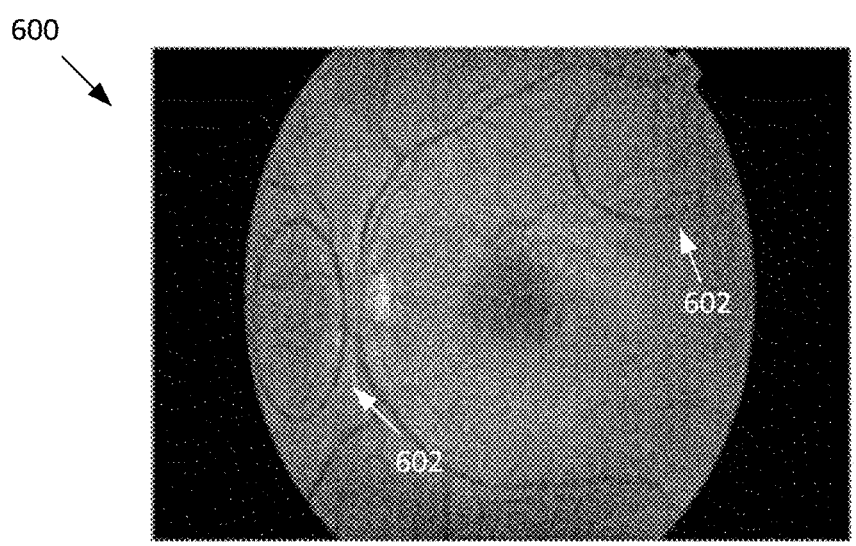
FIG. 6 is a detailed image of a fundus that includes macular edema.
Figure 7:
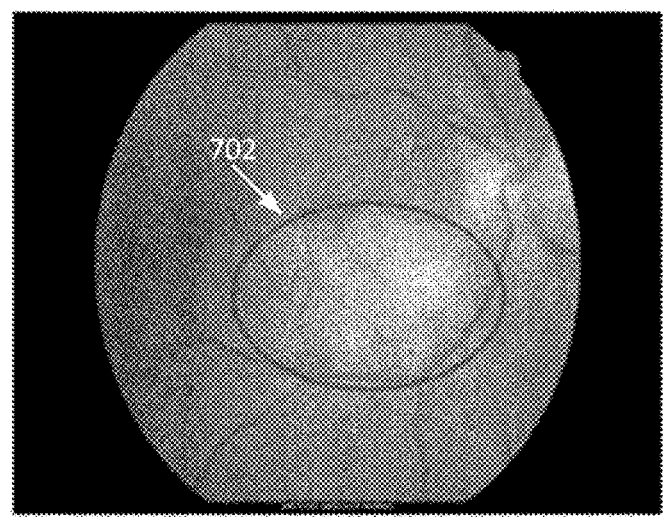
FIG. 7 is a detailed image of a fundus that includes ischemic spots.
Figure 8:
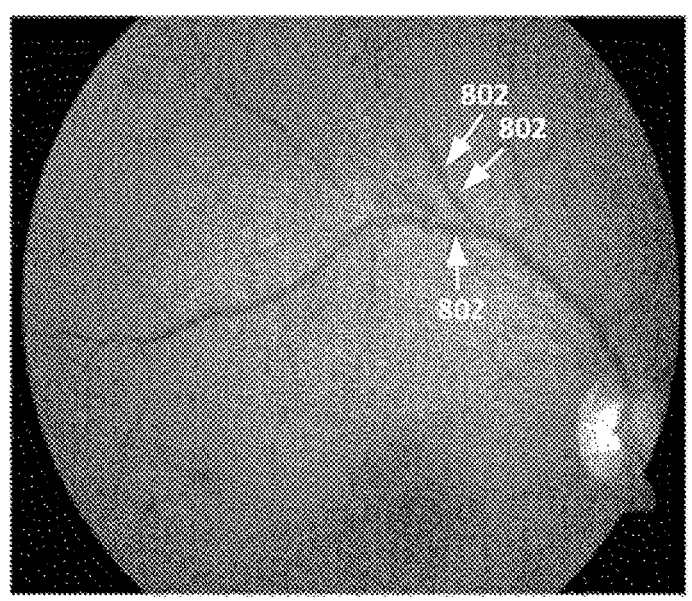
FIG. 8 is a detailed image of a fundus that includes micro-aneurysms.

FIG. 5 is a detailed image of a fundus 500 that includes micro-hemorrhages 502, which are shown as red spots. FIG. 6 is a detailed image of a fundus 600 that includes macular edema 602 which are shown as dark shadows. FIG. 7 is a detailed image of a fundus 700 that includes ischemic spots 702 shown as white patches. FIG. 8 is a detailed image of a fundus 800 that includes micro-aneurysms 802 shown as "beading" along vessel walls. During sepsis, the fundus experiences micro hemorrhages, micro aneurysms, structural changes in the vessels (e.g., vessel diameters and lumen to wall thickness ratios, tissue perfusion heterogeneity, local tissue oxygenation differences, microvascular clotting, and extravascular fluid (edema).

For patients with no indication of fundus microvascular dysregulation, clinicians may conduct additional fundus screenings and provide precautionary sepsis care. The clinicians may also investigate other possible causes for decreased heart rate variability and/or skin surface temperature irregularities. For patients with indications of fundus microvascular dysregulation, the analysis engine 220 provides an estimate of the sepsis progression level. Guidelines for sepsis treatment at the estimated progression level can also be provided. In both cases with and without indications of fundus microvascular dysregulation, microvascular dysregulation scores are trended for further analysis to improve the deep learning algorithm. Additionally, the analysis engine 220 can use the microvascular dysregulation scores to create a sepsis risk index.

The acquisition and scoring of the fundus images can leverage an existing network, such as the RetinaVue® network available from Welch Allyn Inc., Skaneateles Falls, NY. Initially, clinicians grade the microvascular dysregulation. The grades, along with diagnoses and results, are then used as inputs for machine learning and the deep learning algorithm.

In a further example embodiment, the system 200 can be configured to include automatic measurement of the flicker response. Due to normal chemical cascades in the retina, a flashing light dilates small capillaries and arterioles in a predictable way. The system 200 can be configured to measure the reactivity of the retinal blood vessels which are diminished in septic patients due to neurovascular decoupling. Additionally, the system 200 can be configured to compare sizes of capillaries with light flicker and without.

In another example embodiment, the system 200 can be configured to measure local oxygenation of the retina by measuring tissue pallor of the retina because perfusion abnormalities at the microvascular level occur in septic patients. In this example embodiment, the system 200 can be configured to compare a library of normal-pallor retinas to that of a patient who is undergoing sepsis screening.

In a further example embodiment, the system 200 can be configured to measure blood flow velocity changes because blood vessel walls become "sticky" and blood cells become rigid causing sluggish blood flow in septic patients.

In a further embodiment, the system 200 can be configured to use algorithms to measure blood vessel diameters and lumen to wall thickness ratios which change in response to dysregulated vasomotor reactions in septic patients.

Microvascular changes in septic patients that are observed in the sublingual beds under the tongue may also be visible in the retina. For example, microvascular changes observed in the retina that can be used for sepsis screening can include visible structural changes in the vessel (e.g., vessel diameters and lumen-wall thickness ratios will change in response to dysregulated vasomotor reactions), micro-aneurysms (e.g., caused by vessel wall weakness and sudden pressure changes), perfusion heterogeneity (e.g., the population of perfused vessels will decrease and will be highly variable, with normally perfused and non-perfused, engorged, and intermittently flowing vessels all within the same capillary beds), change in blood volume flow velocities (e.g., the vessel walls become sticky and the blood cells become less able to morph their shapes to accommodate the vessels), local tissue oxygenation decreases causing pallor (e.g., this occurs as oxygen transport and diffusion are disrupted by the microvascular changes), microvascular clotting caused by the hyper-coagulation state of sepsis (disseminated intravascular clotting), extravascular fluid/edema (prevalent due to the increased permeability of the damaged endothelium of the capillary walls), and the like.

In a further embodiment, the system 200 measures the degree of endothelial dysfunction along with vital signs data related to endothelial performance. For example, the system 200 can take into consideration additional vital signs parameters such as acute inflammatory response, vascular permeability, intravascular coagulation, local $O_2$ hypoxia, total blood flow compared to normal blood flow, and the like. These additional vital signs data are measured using a fast, easy to use, real time, and non-invasive measurement device with automatic data analysis and trending capabilities.

Additionally, the system 200 can be used to perform intra-ocular pressure measurement which can increase in septic patients and where there can be a positive correlation with inflammatory biomarkers. The system 200 can also incorporate a flicker response measurement for vascular reactivity changes because the ability of the blood vessels to dilate and constrict in response to the normal regulatory chemical cascades dramatically diminishes in septic patients. The eye offers an easy way to assess vascular reactivity due to the neurovascular coupling in the retina when a flickering light dilates small capillaries and small arterioles. This can mirror the vascular reactivity in the rest of the body and therefore help guide caregivers in fluid management for septic patients.

Referring now to FIG. 1, if microvascular irregularity/dysregulation is not detected (Step 106), the method 100 returns to measuring vital signs (Step 102). If microvascular irregularity/dysregulation is detected (Step 106), the patient is screened as having sepsis and the method 100 proceeds to provide sepsis treatment (Step 108).

In certain example embodiments, the system 200 in addition to being used as a diagnostic tool, is also used to monitor a septic patient's microvascular status during sepsis treatment by looking at captured fundus images of the eye.

In another example embodiment, non-invasive measurements are obtained to screen for sepsis in Step 104 by comparing photoplethysmogram (PPG), bio-impedance, or other non-invasive perfusion measurements such as $StO_2$ after a stimulus has been applied to the skin of the patient. During early onset of sepsis, vasodilation (e.g., the dilatation of blood vessels) occurs at the endothelial level. The amplitude differential between these non-invasive perfusion measurements in response to the stimulus will be less in septic patients than the amplitude differential in non-septic patients who have normal endothelial function.

Figure 9:
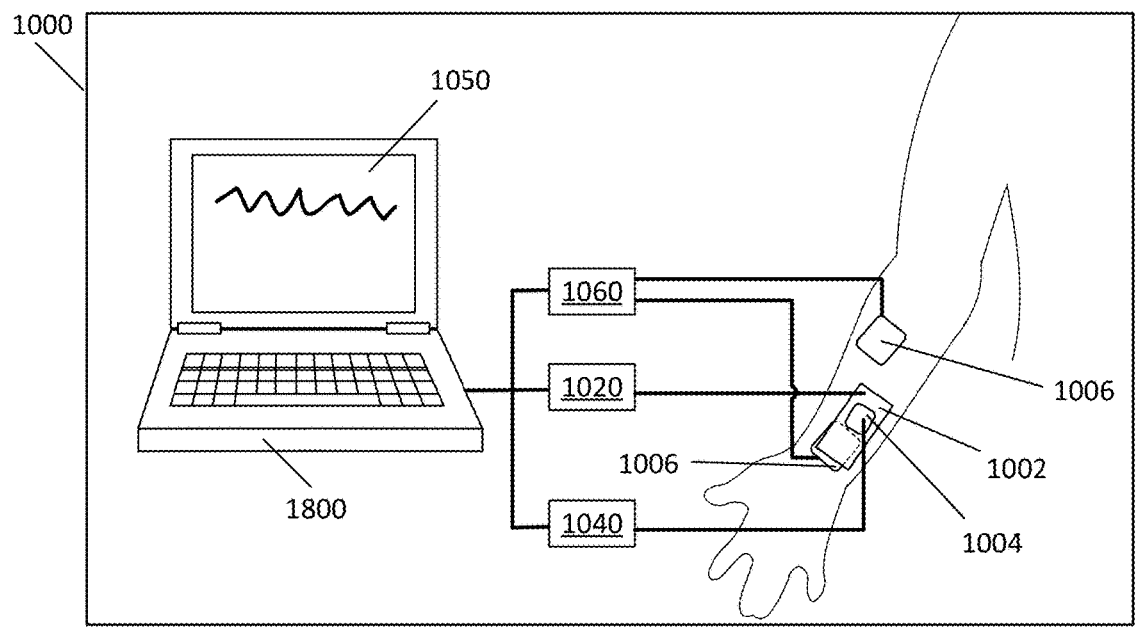
FIG. 9 schematically illustrates a system for measuring microvascular response.

FIG. 9 schematically illustrates an example system 1000 for measuring microvascular response to a stimulus in accordance with the example embodiment described in the previous paragraph. The system 1000 includes a sensor device 1002 to deliver a range of temperatures to the skin. In one embodiment, the system 1000 uses a PPG sensor 1004 controlled by a PPG module 1040. In another embodiment, the system 1000 uses an impedance sensor 1006 controlled by a impedance module 1060. The same sensor device 1002 can be used for both embodiments, and each embodiment is configured to evaluate the vascular response to the induced temperature changes. In practice, the PPG sensor 1004 and impedance sensor 1006 are not used together at the same time in the system 1000. However, the system 1000 is capable of using both types of sensors since both use the same sensor device 1002 and the signals would not interfere with each other.

The system 1000 further includes a computing device 1800, which is described in more detail with reference to FIG. 22. Also, the system 1000 includes a screen 1050.

The system 1000 monitors the condition of the vasculature underneath the sensor device 1002. As described above, two alternative embodiments can be used to noninvasively evaluate the pulsating blood flow near and underneath the sensor device 1002. Current pulse amplitudes are measured as the underlying vasculature expands and contracts with the beating of the heart. As the arteries constrict, there is less blood flow and therefore smaller or no measurable cardiac pulsations. The amplitude of the pulsations while the skin is warmed are compared to the amplitude of the pulsations when the skin is cooled. A "normal" difference in pulse amplitude when the warmed pulses are compared to the cooled pulses can be established by measuring a plurality of patients. The normal difference indicates a normal endothelial function that produces a dramatic change in pulse heights for the different temperatures induced by the sensor device 1002, and less or no pulse height difference is observed on septic patients whose endothelial function is compromised.

Figure 10:
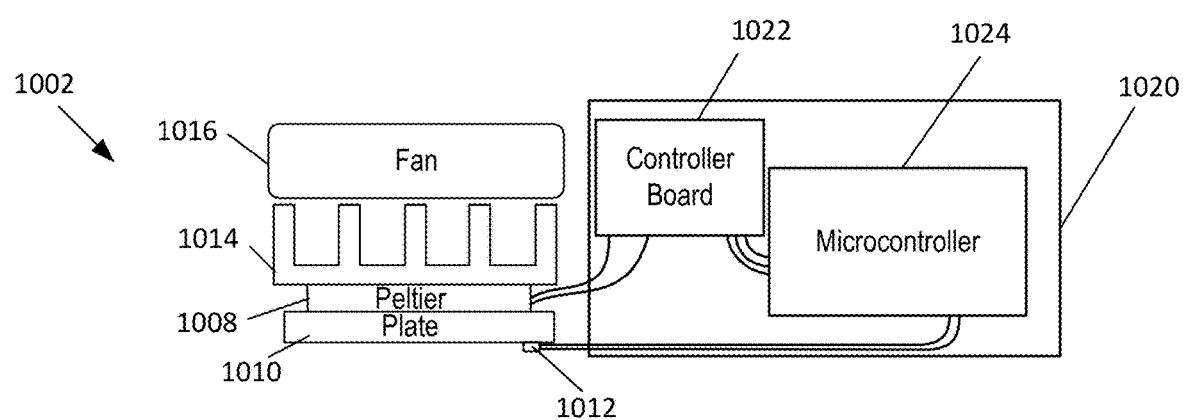
FIG. 10 schematically illustrates a temperature induction device.

FIG. 10 schematically illustrates the sensor device 1002. The sensor device 1002 includes a Peltier heater cooler 1008 that is configured to turn an electrical current into temperature. Depending on the direction (e.g., polarity) of the electrical current, one side of the Peltier heater cooler 1008 gets warm while the other side gets cool.

A plate 1010 is mounted onto the Peltier heater cooler 1008. The plate 1010 operates to evenly distribute the induced temperature from the Peltier heater cooler 1008. The plate 1010 also provides a machine-readable surface. For example, the PPG sensor 1004 or the impedance sensor 1006 can be embedded in the plate 1010. In some examples, the plate 1010 is made from aluminum or similar alloy. The plate 1010 can have a thickness of about ⅛ inches, and a surface area of about 1 square inch.

The sensor device 1002 also includes a monitoring thermistor 1012 that is thermally connected to the plate 1010. The monitoring thermistor 1012 provides inputs for a control algorithm stored inside a temperature module 1020 (see also FIG. 9). The monitoring thermistor 1012 is a high accuracy thermistor that monitors the temperature of the plate 1010 and feeds that information to the control algorithm.

The sensor device 1002 further includes a heatsink 1014 and a fan 1016 connected to the heatsink 1014. The heatsink 1014 and fan 1016 are used to return the sensor device 1002 to room temperature.

Figure 11:
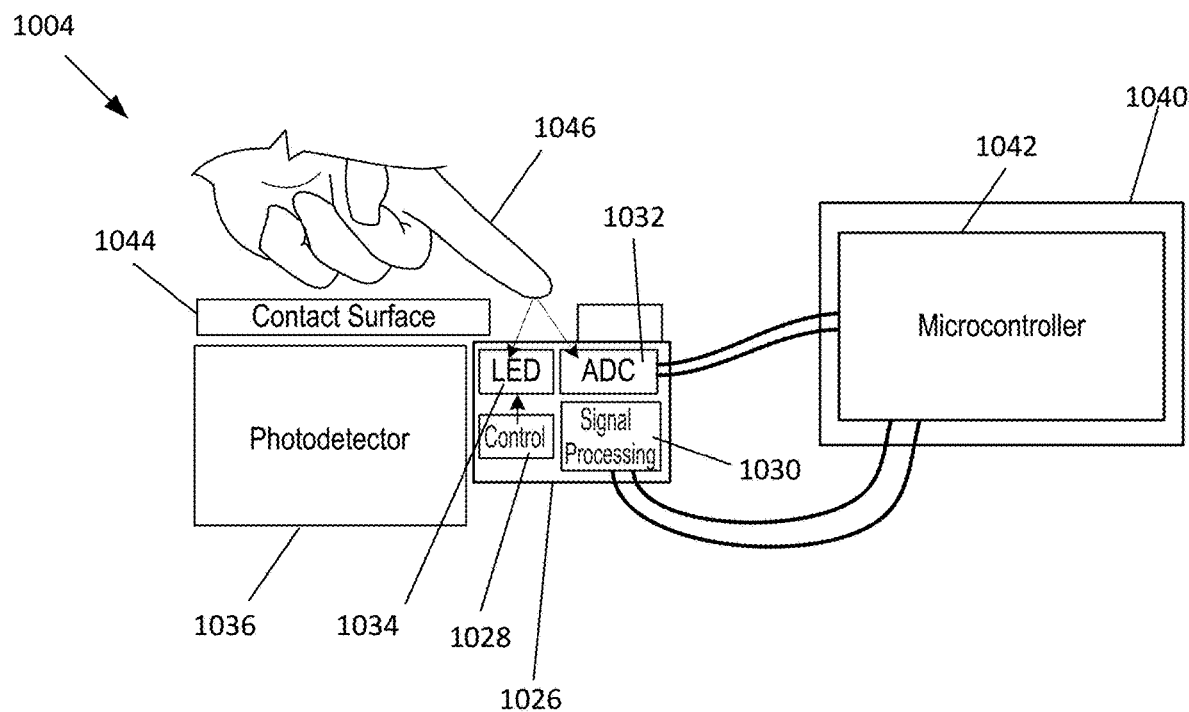
FIG. 11 schematically illustrates a PPG sensor.

Referring now to FIGS. 9-11, the system 1000 includes a temperature module 1020 connected to the sensor device 1002. The temperature module 1020 controls the heat generated on one side and the cold generated on the opposite side of the sensor device 1002 in proportion to the voltage applied to the device. Changing the polarity of the voltage will change the hot and cold sides. The temperature module 1020 has a controller board 1022 that allows simple control over the polarity and the pulse width modulation of the voltage going to the sensor device 1002.

The controller board is driven by a microcontroller 1024. A pulse width modulation output from the microcontroller 1024 is used to control the amount of power and the polarity of the voltage going to the sensor device 1002. The microcontroller 1024 includes the control algorithm that is used to control the sensor device 1002.

The control algorithm controls the sensor device 1002 so that only warm and cool temperatures are generated. This is done to avoid temperatures that are uncomfortable for a patient. For example, a warm temperature of about 40° C. and a cool temperature of about 18° C. are generated by the sensor device 1002 for the PPG and impedance sensors 1004, 1006 to measure microvascular responses.

FIG. 11 schematically illustrates the PPG sensor 1004 controlled by the PPG module 1040. A photoplethysmogram (PPG) signal is used to detect blood volume changes in a microvascular bed of tissue. The PPG sensor 1004 includes an analog front end chip 1026 and a photodetector 1036 that are surrounded by a thermally conductive contact surface 1044. The analog front end chip 1026 includes a control module 1028, a signal processing module 1030, an analog-to-digital-converter (ADC) 1032, and light emitting diodes (LEDs) 1034. In certain examples, the LEDs 1034 include infra-red (IR), red, and green LEDs. The analog front end chip 1026 communicates with a microcontroller 1042 in the PPG module 1040 via a bidirectional two-wired serial (I2C) bus. In some examples, the microcontroller 1042 in the PPG module 1040 and the microcontroller 1024 in the temperature module 1020 are the same component.

As shown in FIG. 11, a skin surface 1046 such as the tip of a finger can be placed on the thermally conductive contact surface 1044 of the PPG sensor 1004. The analog front end chip 1026 amplifies and controls the light emitted from the LEDs 1034. The analog front end chip 1026 also processes analog PPG signal data from the photodetector 1036. The PPG signal data is a measurement of the absorption of the light emitted from the LEDs 1034 by the skin surface 1046. The PPG module 1040 uses the PPG signal data from the photodetector 1036 to measure the microvascular response near the skin surface 1046 after heating and cooling the skin surface 1046 by the sensor device 1002. The microvascular response can be displayed on a screen 1050 connected to the PPG module 1040 (see FIG. 9).

Figure 12:
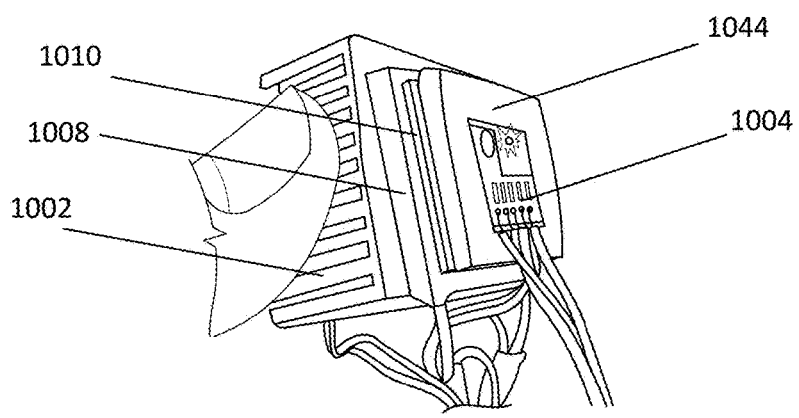
FIG. 12 illustrates a PPG sensor attached to a temperature induction device.

FIG. 12 illustrates a prototype of the PPG sensor 1004 surrounded by the thermally conductive contact surface 1044, and attached to the sensor device 1002. The Peltier heater cooler 1008 is mounted onto the sensor device 1002, and the plate 1010 is mounted on the Peltier heater cooler 1008. The thermally conductive contact surface 1044 is mounted over the plate 1010 and surrounds the PPG sensor 1004.

Figure 13:
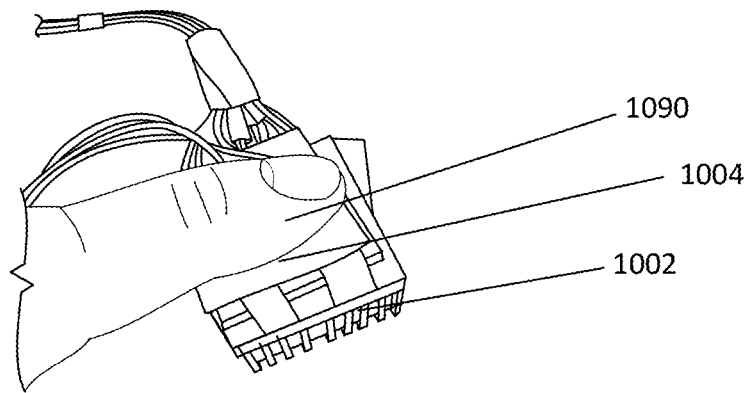
FIG. 13 illustrates a PPG sensor and temperature induction device in use.
Figure 14:
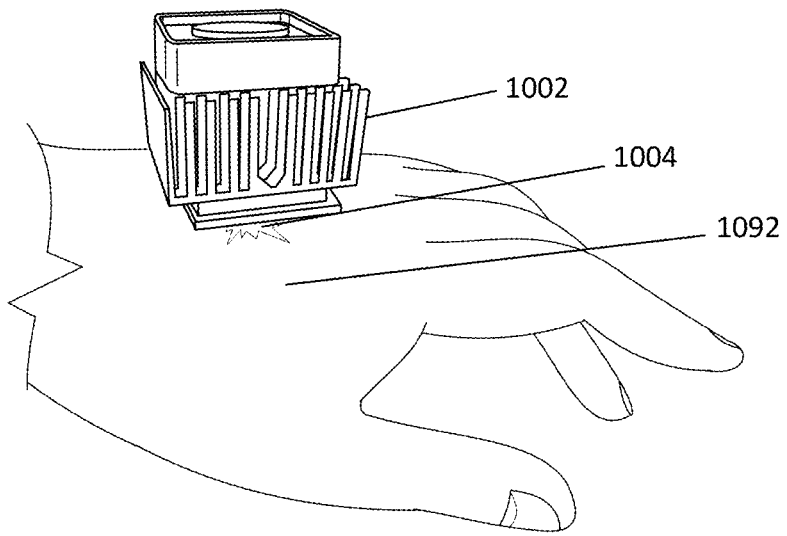
FIG. 14 illustrates another PPG sensor and temperature induction device in use.

FIG. 13 illustrates the PPG sensor 1004 and the sensor device 1002 in use for collecting PPG waveform data on an index finger 1090. FIG. 14 illustrates the PPG sensor 1004 and the sensor device 1002 in use for collecting PPG waveform data on a surface 1092 on the back of a hand. As shown in FIGS. 13 and 14, the sensor device 1002 and PPG sensor 1004 can be used on various skin surfaces.

Figure 15:
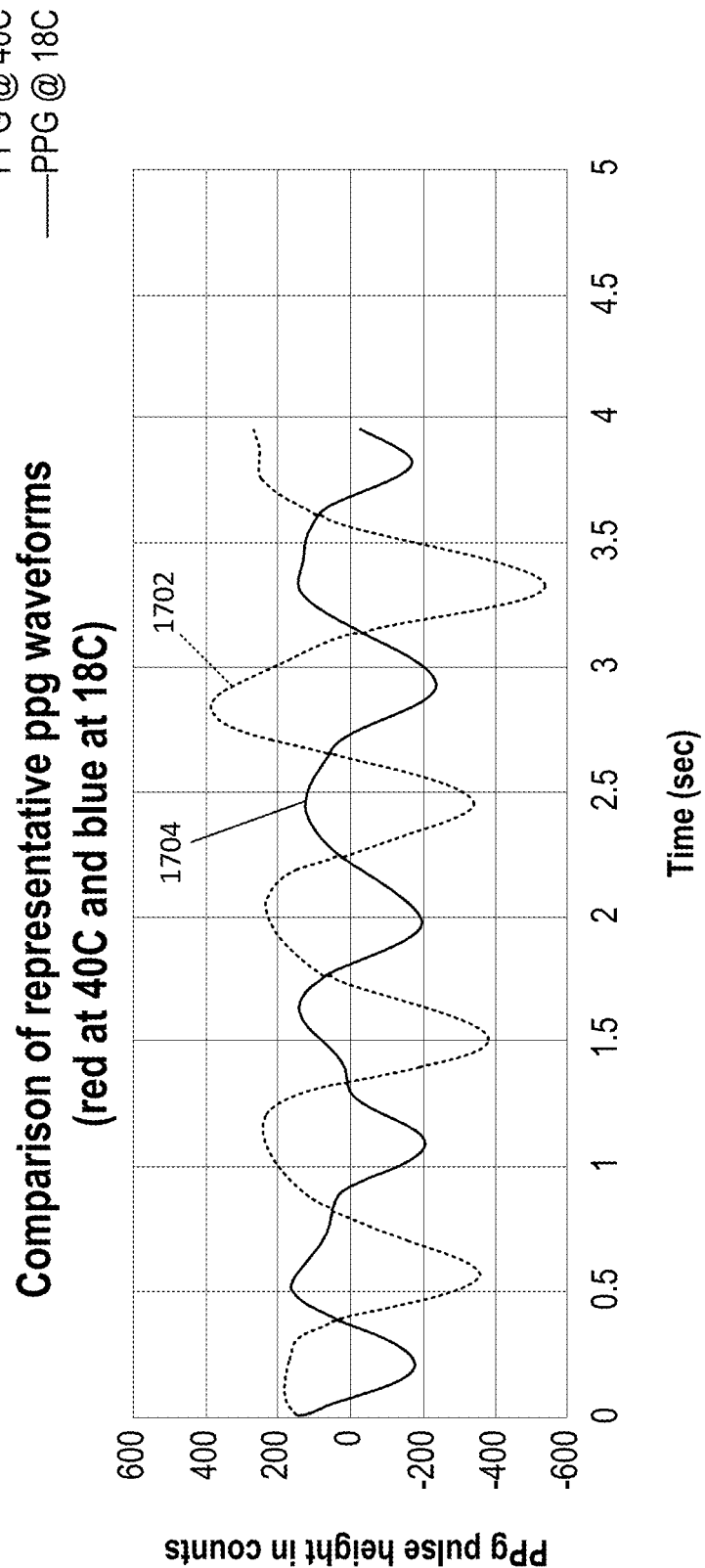
FIG. 15 is a graph illustrating two sets of data collected by a PPG sensor.

FIG. 15 is a graph illustrating two sets of data collected by the PPG sensor 1004. Each set of data was acquired at a different temperature induced by the sensor device 1002. A first set of data 1702 was collected at 40° C. and a second set of data 1704 was collected at 18° C. As shown in FIG. 15, the PPG amplitudes of the first set of data 1702 are larger than the PPG amplitudes of the second set of data 1704. Thus, the first and second sets of data 1702, 1704 indicate a normal microvascular response because the temperature difference (warm vs. cool) is shown to have an effect on blood flow. In septic patients, the difference in the PPG amplitudes between the first and second sets of data 1702, 1704 would be less because of vasodilation which reduces the microvascular response. Thus, by comparing the first set of data 1702 and the second set of data 1704, the system 1000 can screen for sepsis.

In an alternative example embodiment, tissue oxygenation $StO_2$ can be measured to determine the microvascular response following a thermal stimulus from the sensor device 1002. For example, the change in $StO_2$ can be measured after a heat pulse is sent to a skin surface (e.g., on the hand). Similarly, the change in $StO_2$ can be measured after a cold pulse is sent to a skin surface. The system 1000 is configurable for measuring $StO_2$. For example, the system 1000 can use the LEDs 1034 as a near infrared light source to illuminate the skin surface after a temperature pulse has been sent to the skin surface, and use the photodetector 1036 to detect reflected light to measure $StO_2$.

Figure 16:
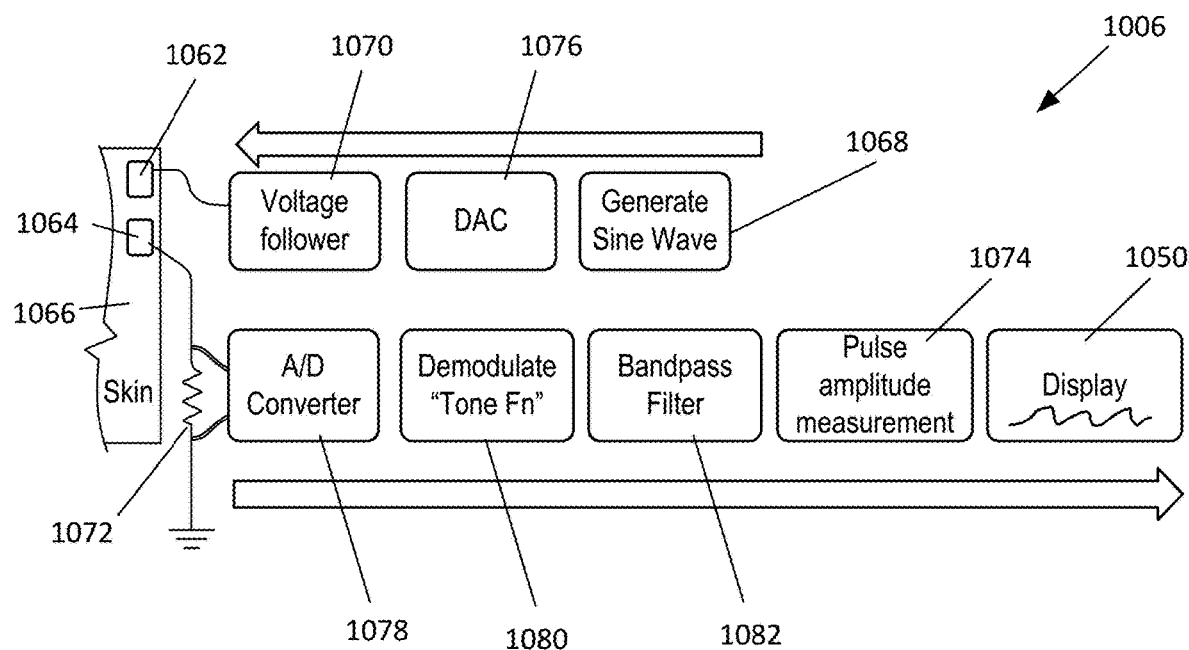
FIG. 16 schematically illustrates an impedance sensor.

FIG. 16 schematically illustrates the impedance sensor 1006. As shown in FIG. 16, the impedance sensor 1006 includes electrodes 1062, 1064 that attach to a skin surface 1066. In some examples, the skin surface 1066 is the same area as the skin surface 1046 in FIG. 11. In other examples, the skin surfaces 1046, 1066 are located on different areas of a patient's body.

A signal generator 1068 is configured to produce a sinewave of amplitudes up to +/−10 Volts. In one example, the impedance sensor 1006 is configured to generate an 8000 Hz sinewave for the excitation signal. An amplifier 1070 is used in a voltage follower configuration to increase the current sourcing capability of the signal up to 20 mA. A digital-to-analog-converter (DAC) processes the signal generated by the signal generator 1068 before the signal is amplified by the amplifier 1070, and before the signal reaches the skin surface 1066.

The excitation signal runs from the first electrode 1062 to the second electrode 1064 through the skin surface 1066, and through a reference resistor 1072 to ground. In some examples, the impedance sensor 1006 includes an analog-to-digital-converter (ADC) 1078, a demodulator 1080, and a bandpass filter 1082 to process the voltage obtained from the reference resistor 1072. The processed voltage from the reference resistor 1072 is measured by a data acquisition module 1074, and an impedance is calculated from the voltage measurement. In some examples, the data acquisition module 1074 and the control circuitry that controls the sinewave amplitudes generated by the electrodes 1062, 1064 are included in the impedance module 1060.

By measuring the electrical impedance under the skin surface 1066, it is possible to determine the microvascular response after heating and cooling the skin surface 1066 by the sensor device 1002. In some examples, the microvascular response is displayed on a screen 1050 connected to the impedance module 1060 (see FIG. 9).

Figure 17:
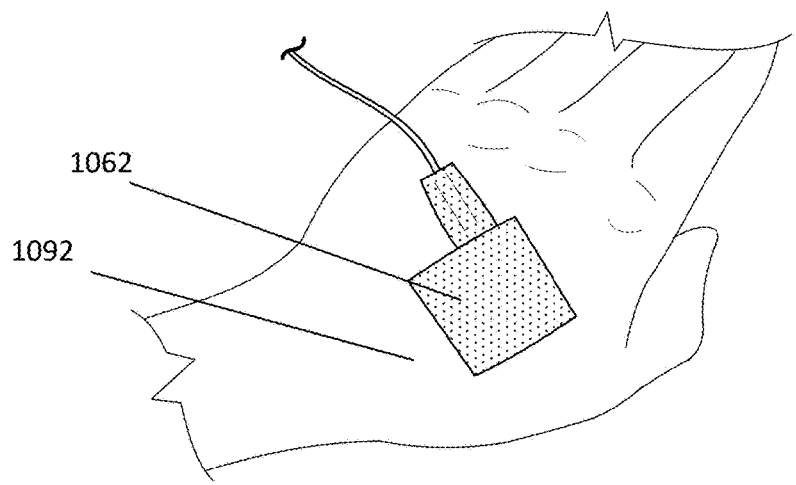
FIG. 17 shows a first electrode of an impedance sensor.

FIG. 17 shows a first electrode 1062 of the impedance sensor 1006 attached to a skin surface 1092 on the back of a hand. The first electrode 1062 is trimmed to the outline of the sensor device 1002. The first electrode 1062 is reusable.

Figure 18:
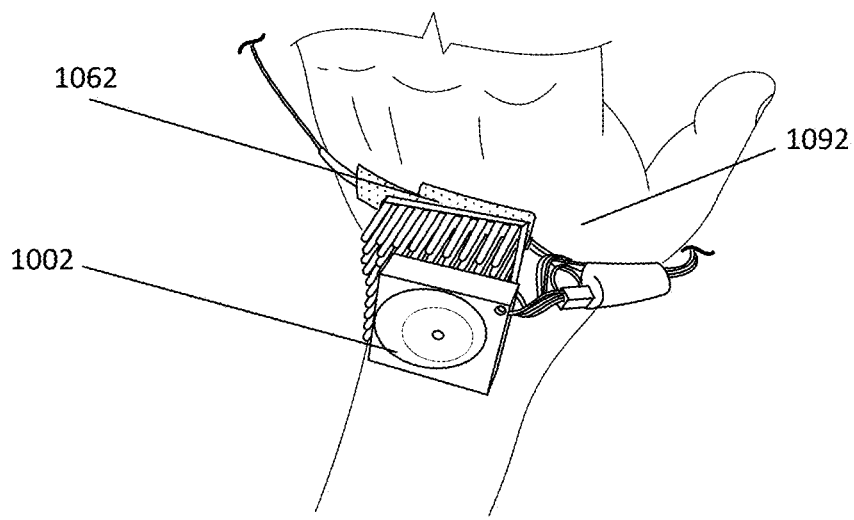
FIG. 18 shows a temperature induction device attached to an impedance electrode.

FIG. 18 shows the sensor device 1002 attached to the electrode 1062. In one embodiment, a thermally conductive two-sided tape is used to attach the sensor device 1002 to the electrode 1062. Additional means to attach the sensor device 1002 are possible.

Figure 19:
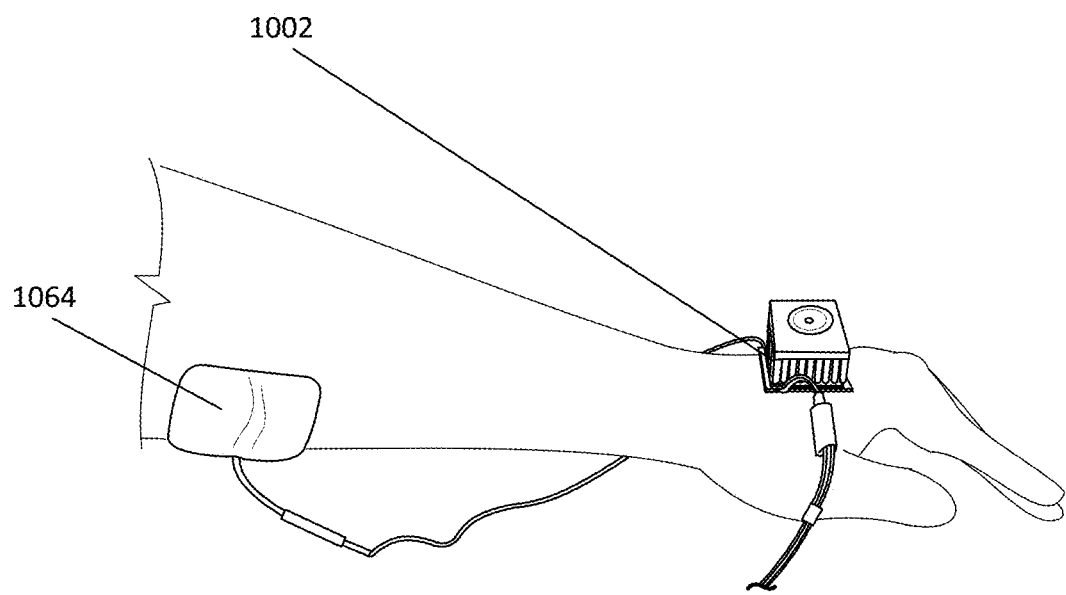
FIG. 19 shows a second electrode of an impedance sensor.

FIG. 19 shows a second electrode 1064 of the impedance sensor 1006 attached to a skin surface near the elbow of a patient. The second electrode 1064 is also reusable. It is contemplated that multiple impedance electrodes can be added at different distances so that impedance can be measured at different tissue depths.

Figure 20:
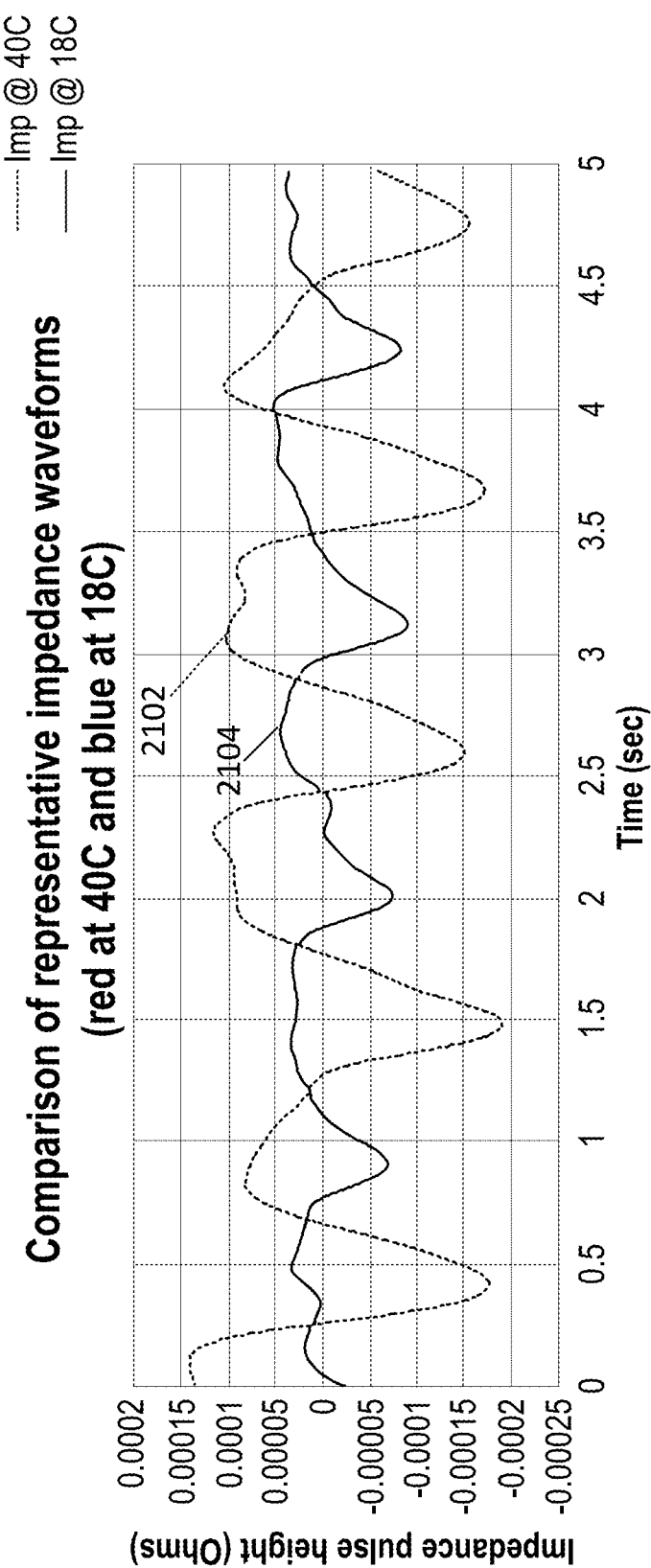
FIG. 20 is a graph illustrating two sets of data collected by an impedance sensor.

FIG. 20 is a graph illustrating two sets of data collected by the impedance sensor 1006. Each set of data was acquired at a different temperature induced by the sensor device 1002. A first set of data 2102 was collected at 40° C. and a second set of data 2104 was collected at 18° C. As shown in FIG. 20, the pulse amplitudes of the first set of data 2102 are larger than the pulse amplitudes of the second set of data 2104. Thus, the first and second sets of data 2102, 2104 indicate a normal microvascular response because the temperature difference is shown to have an effect on blood flow. In septic patients, the difference between the pulse amplitudes in the first and second sets of data 2102, 2104 would be less because of vasodilation which reduces the microvascular response. Thus, by comparing the first set of data 2102 and the second set of data 2104, the system 1000 can screen for sepsis.

In another example, a phase difference between the driving signal and the detected signal is measured to determine microvascular response. In a further example, a complex impedance over a range of frequencies is measured instead of a magnitude at a single frequency. In another example, an array of impedance sensors is used to measure impedance over different regions of the skin that may show different characteristics over different frequencies and temperatures. Also, in addition to the measuring the difference in amplitude values measured over different induced temperatures (e.g., warm vs. cool), the rate of change in the amplitude values may also be measured to obtain a dynamic measure of microvascular response.

Also, additional types of non-invasive stimuli can be used to measure microvascular response. In one alternative example, instead of using induced temperature changes, a nitroglycerin patch is used to relax and widen the blood vessels of a patient. In this example, the PPG sensor 1004 or the impedance sensor 1006 are used to measure the microvascular response after the nitroglycerin patch has been applied to the patient. As with the examples described above that use induced temperature changes, the amplitude differential between the measurements in response to the nitroglycerin patch will be less in septic patients than the amplitude differential measured in non-septic patients due to vasodilation.

In certain example embodiments, the system 1000 in addition to being used as a diagnostic tool, is also used to monitor a septic patient's microvascular status during sepsis treatment by measuring the septic patient's microvascular response to stimuli.

Referring now to FIG. 1, if irregularities in the microvascular response to the stimulus are not detected (Step 106), the method 100 returns to measuring vital signs (Step 102). If irregularities in the microvascular response to the stimulus are detected (Step 106), the patient is screened as having sepsis and the method 100 proceeds to provide sepsis treatment (Step 108).

Sepsis treatment (Step 108) typically includes antibiotics, fluid resuscitation, and if necessary, vasopressors. Fluid resuscitation is an infusion of IV fluids such as crystalloid fluids. If the septic patient's condition does not improve, vasopressors are administered which are pharmaceutical drugs that cause blood vessels to construct to drive up blood pressure.

Once a patient is screened as septic, the method 100 obtains additional non-invasive measurements during treatment (Step 110), and then uses the additional non-invasive measurements to determine whether the patient is responding to the treatment (Step 112). By determining whether a patient is responding to the treatment, a clinician can modify, escalate, de-escalate, or even terminate the treatment if it is determined that the patient is no longer septic.

For example, if it is determined that the condition of the septic patient is improving in response to fluid resuscitation ("Yes" in Step 112), the fluid resuscitation treatment continues. If it is determined that the condition of the septic patient is not improving ("No" in Step 112), the method 100 returns to Step 108 and a vasopressor is administered because it is likely that the septic patient will not respond to additional fluid resuscitation, or the septic patient's condition may even worsen in response to additional fluid resuscitation.

Figure 21:
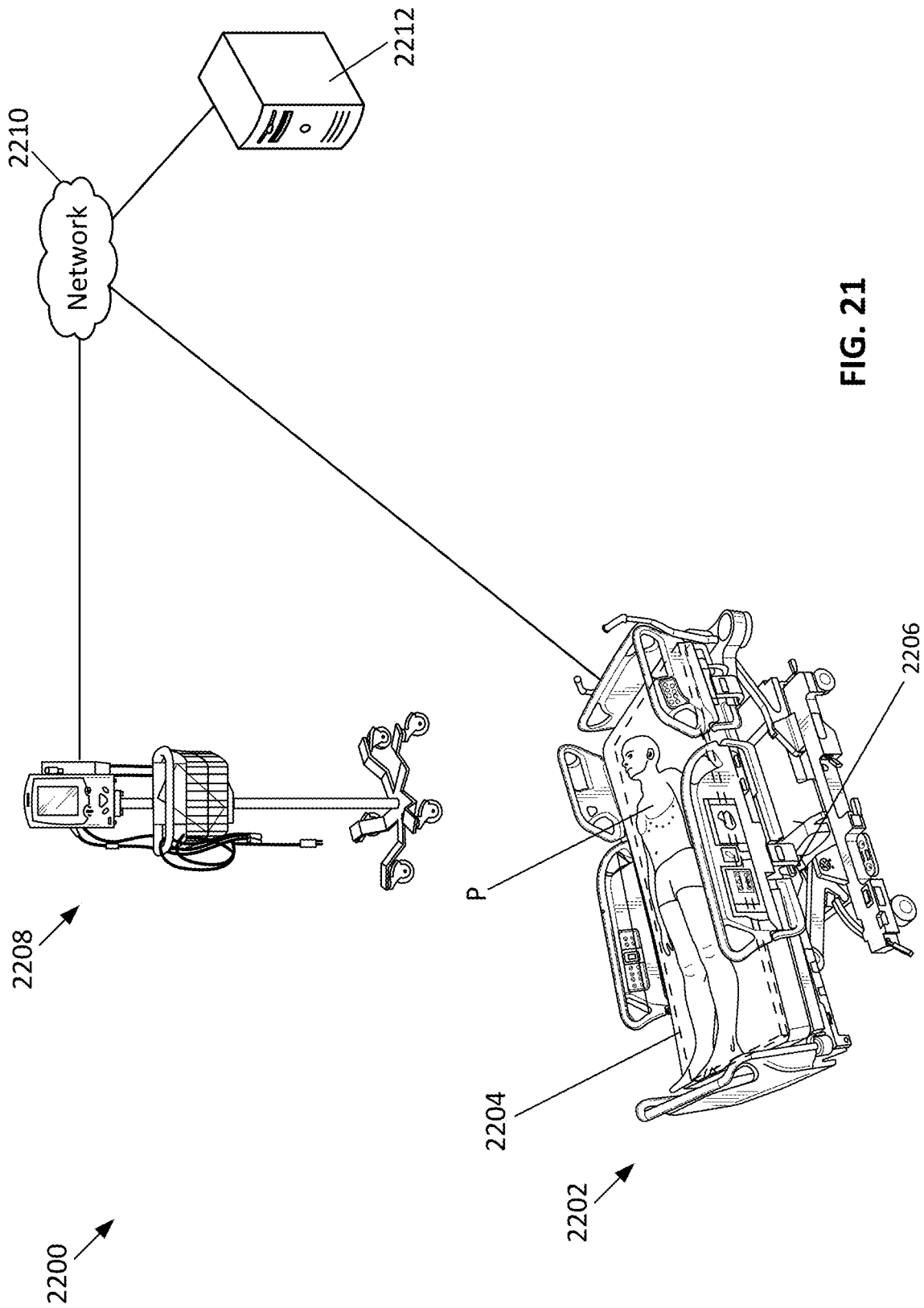
FIG. 21 schematically illustrates a system configured to measure a macrovascular response to sepsis treatment.

FIG. 21 schematically illustrates a system 2200 configured to obtain non-invasive measurements (Step 110) during sepsis treatment. As an illustrative example, the non-invasive measurements are used to determine whether a septic patient P is responding to fluid resuscitation treatment (Step 112). The system 2200 monitors macrovascular response during sepsis treatment by measuring non-invasive vital sign measurements after applying a stimulus.

The system 2200 measures changes in vital sign measurements detected before and after an extremity of the septic patient P is tilted upward. The response in septic patients who are responding to fluid resuscitation will be different from the response in septic patients who are not responding to the fluid resuscitation treatment. By automating this process, the system 2200 provides a repeatable measurement that removes the burden of manual testing.

As shown in FIG. 21, the system 2200 includes a patient support device 2202. In some examples, the patient support device 2202 is a hospital bed, lift, or surgical table. In a preferred example, the patient support device 2202 is a hospital bed.

The patient support device 2202 includes a frame 2204 connected to a motor 2206 such that the frame 2204 is configured to move up and down, and to be tilted at an angle relative to the ground by the motor 2206. For example, an upper portion of the frame 2204 can be tilted to raise the upper body and head of the septic patient P. Also, a lower portion of the frame 2204 can be tilted to raise a lower extremity such as the legs of the septic patient P.

The system 2200 further includes a medical device 2208 that is configured to measure one or more vital signs. In some examples, the medical device 2208 is a vital signs monitor such as a Connex® spot monitor available from Welch Allyn Inc., Skaneateles Falls.

The medical device 2208 communicates with a control device 2212 via a network 2210. The network 2210 is substantially similar to the network 210 described above. The control device 2212 includes the computing device 1800 described in more detail with reference to FIG. 22. The control device 2212 operates to control the medical device 2208 to automatically record vital sign measurements and to receive the vital sign measures obtained from the medical device 2208. Also, the control device 2212 further operates to control the motor 2206 of the patient support device 2202 to tilt the frame 2204 at an angle relative to the ground.

The system 2200 automates a process for determining the septic patient P's response to fluid resuscitation treatment. The system 2200 is configured to raise an extremity of the septic patient P so that blood flows to the septic patient P's heart, and to non-invasively measure one or more vital signs before and after the extremity is raised. The vital sign measurements are used to determine a response to the fluid shift away from the extremity and toward the heart.

In one example embodiment, the control device 2212 causes the system 2200 to receive a first vital sign measurement when the frame 2204 is in the rested position, receive a second vital sign measurement when the frame 2204 is in the tilted positon, and compare the first and second vital sign measurements to determine whether the septic patient P is improving.

The system 2200 tilts a portion of the frame 2204 of the patient support device 2202 from a rested position to a tilted position, and uses the medical device 2208 to obtain non-invasive vital sign measurements before and after the frame 2204 is tilted. For example, the system 2200 tilts a lower portion of the frame 2204 to raise the leg of the septic patient P. In one example, the system 2200 tilts the lower portion of the frame 2204 by about 45° relative to the ground. By tilting the lower portion of the frame 2204, blood will flow from the leg toward the patient P's heart. The non-invasive vital sign measurements obtained by the medical device 2208 may include heart rate, stroke volume, cardiac output (e.g., the product of the heart rate and the stroke volume), blood pressure, mean arterial pressure (MAP), and the like.

In one example embodiment, the system 2200 is automated such that the control device 2212 operates to control the frame 2204 to tilt the extremity at predetermined intervals, and further operates to control the medical device 2208 to automatically measure the vital signs of the septic patient P before and after each predetermined interval. The control device 2212 can obtain the automated vital sign measurements without clinician involvement. The control device 2212 trends the automated vital sign measurements over time and uses an algorithm to determine a macrovascular response, and the macrovascular response is used to determine whether the septic patient P's condition is improving in response to the fluid resuscitation treatment.

Accordingly, the system 2200 mobilizes blood in the extremities of the septic patient P to determine whether the septic patient P is positively responding to the fluid resuscitation treatment. If it is determined in Step 112 that the septic patient P is not responding to the fluid resuscitation treatment, the fluid resuscitation treatment is terminated, and a more aggressive treatment such as administering vasopressors to the septic patient P is performed. If it is determined in Step 112 that the status of the septic patient P is improving, the fluid resuscitation treatment can continue or be terminated once the patient is cured (Step 114).

Advantageously, the system 2200 provides automation and objective measurements of the septic patient P's response to fluid resuscitation treatment, and thereby improves the accuracy of determining a septic patient's response to fluid resuscitation treatment.

In one example embodiment, the system 2200 is used to determine the septic patient P's position on the Frank-Starling curve. In a further example embodiment, the system 2200 provides an indication of whether the fluid in the septic patient P is intravascular or extravascular because a symptom of sepsis is endothelial breakdown at the capillary level causing massive fluid shift to the extravascular tissue (edema), with a failure to resuscitate. The system 2200 is configured to measure rapid (vascular) fluid shifts vs. slower fluid shifts of extravascular tissue bound fluid with an automated leg lift fluid assessment.

Figure 22:
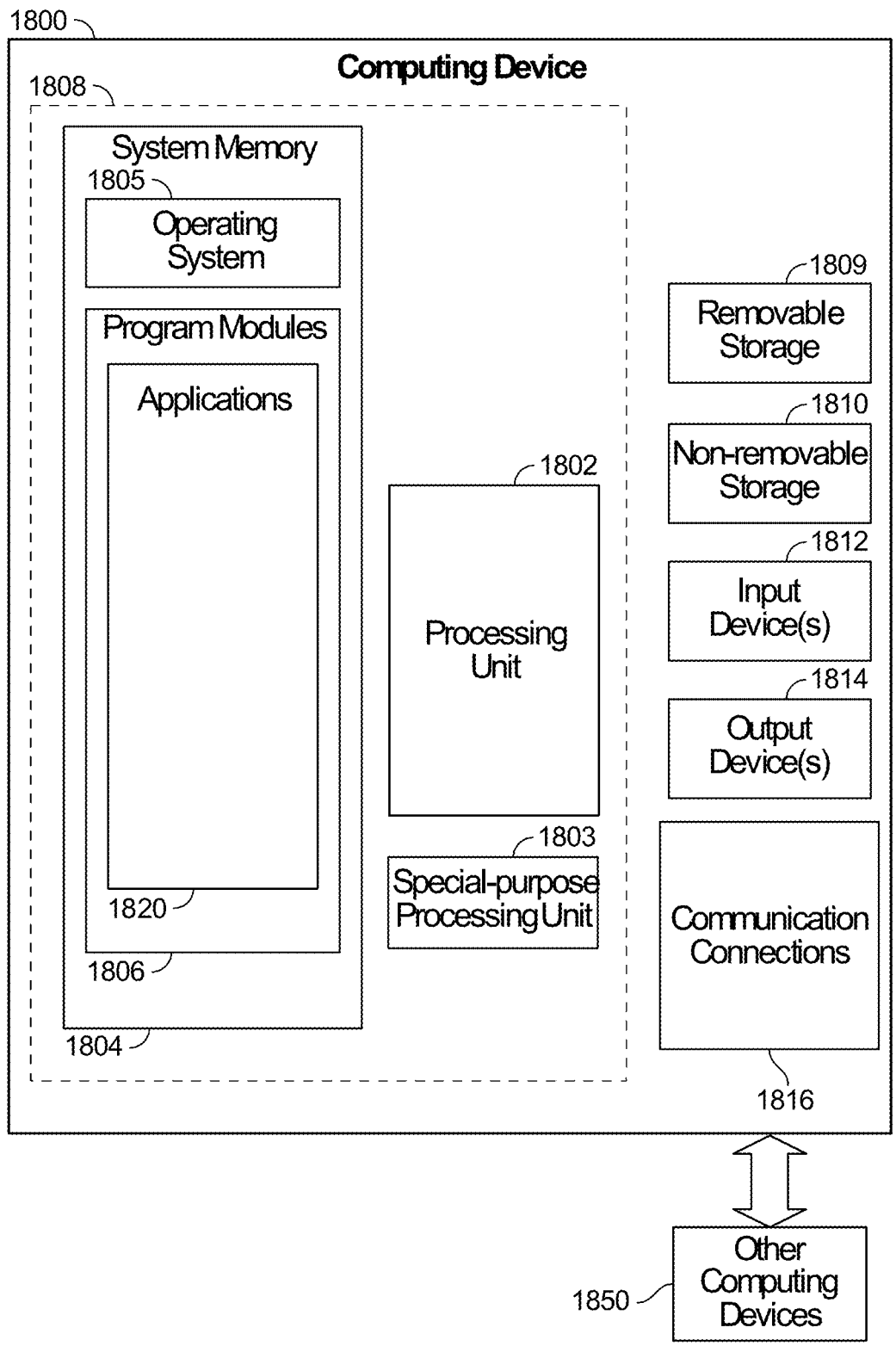
FIG. 22 schematically illustrates an example computing device.

FIG. 22 schematically illustrates the physical components (i.e., hardware) of a computing device 1800 with which embodiments of the disclosure may be practiced. In a basic configuration, the computing device 1800 may include at least one processing unit 1802 and a system memory 1804. Depending on the configuration and type of computing device, the system memory 1804 may comprise, but is not limited to, volatile storage (e.g., random access memory), non-volatile storage (e.g., read-only memory), flash memory, or any combination of such memories. The system memory 1804 may include an operating system 1805 and one or more program modules 1806 suitable for running software applications 1820. The operating system 1805 may be suitable for controlling the operation of the computing device 1800. Embodiments of the disclosure may be practiced in conjunction with a graphics library, other operating systems, or any other application program and is not limited to any particular application or system. This basic configuration is illustrated by those components within a dashed line 1808.

The computing device 1800 may have additional features or functionality. For example, the computing device 1800 may include additional data storage devices (removable and/or non-removable) such as magnetic disks, optical disks, or tape. The additional storage is illustrated by a removable storage device 1809 and a non-removable storage device 1810.

As stated above, a number of program modules and data files may be stored in the system memory 1804. While executing on the at least one processing unit 1802, the program modules 1806 may perform processes including, but not limited to, generate list of devices, broadcast user-friendly name, broadcast transmitter power, determine proximity of wireless computing device, connect with wireless computing device, transfer vital sign data to a patient's EMR, sort list of wireless computing devices within range, and other processes described with reference to the figures as described herein. Other program modules that may be used in accordance with embodiments of the present disclosure, and in particular to generate screen content, may include electronic mail and contacts applications, word processing applications, spreadsheet applications, database applications, slide presentation applications, drawing or computer-aided application programs, etc.

Furthermore, embodiments of the disclosure may be practiced in an electrical circuit comprising discrete electronic elements, packaged or integrated electronic chips containing logic gates, a circuit utilizing a microprocessor, or on a single chip containing electronic elements or microprocessors. For example, embodiments of the disclosure may be practiced via a system-on-a-chip (SOC) where each or many of the components illustrated in FIG. 22 may be integrated onto a single integrated circuit. Such an SOC device may include one or more processing units, graphics units, communications units, system virtualization units and various application functionality all of which are integrated (or "burned") onto the chip substrate as a single integrated circuit. When operating via an SOC, the functionality, described herein, may be operated via application-specific logic integrated with other components of the computing device 1800 on the single integrated circuit (chip). Embodiments of the disclosure may also be practiced using other technologies capable of performing logical operations such as, for example, AND, OR, and NOT, including but not limited to mechanical, optical, fluidic, and quantum technologies. In addition, embodiments of the disclosure may be practiced within a general purpose computer or in any other circuits or systems.

The term computer readable media as used herein may include non-transitory computer storage media. Computer storage media may include volatile and nonvolatile, removable and non-removable media implemented in any method or technology for storage of information, such as computer readable instructions, data structures, or program modules. The system memory 1804, the removable storage device 1809, and the non-removable storage device 1810 are all computer storage media examples (i.e., memory storage.) Computer storage media may include RAM, ROM, electrically erasable read-only memory (EEPROM), flash memory or other memory technology, CD-ROM, digital versatile disks (DVD) or other optical storage, magnetic cassettes, magnetic tape, magnetic disk storage or other magnetic storage devices, or any other article of manufacture which can be used to store information and which can be accessed by the computing device 1800. Any such computer storage media may be part of the computing device 1800. Computer storage media does not include a carrier wave or other propagated or modulated data signal.

The computing device 1800 may also have one or more input devices 1812 such as a keyboard, a mouse, a pen, a sound or voice input device, a touch or swipe input device, and the like. The computing device 1800 may also have one or more output devices 1814 such as a display, speakers, and printer. These devices are examples and others may be used.

The computing device 1800 may include one or more communication connections 1816 allowing communications with other computing devices 1850. Examples of communication connections 1816 include, but are not limited to, RF transmitter, receiver, and/or transceiver circuitry; universal serial bus (USB), parallel, and/or serial ports.

Communication media may be embodied by computer readable instructions, data structures, program modules, or other data in a modulated data signal, such as a carrier wave or other transport mechanism, and includes any information delivery media. The term "modulated data signal" may describe a signal that has one or more characteristics set or changed in such a manner as to encode information in the signal. By way of example, communication media may include wired media such as a wired network or direct-wired connection, and wireless media such as acoustic, radio frequency (RF), infrared, and other wireless media.

Embodiments of the present invention may be utilized in various distributed computing environments where tasks are performed by remote processing devices that are linked through a communications network in a distributed computing environment.

Figure 23:
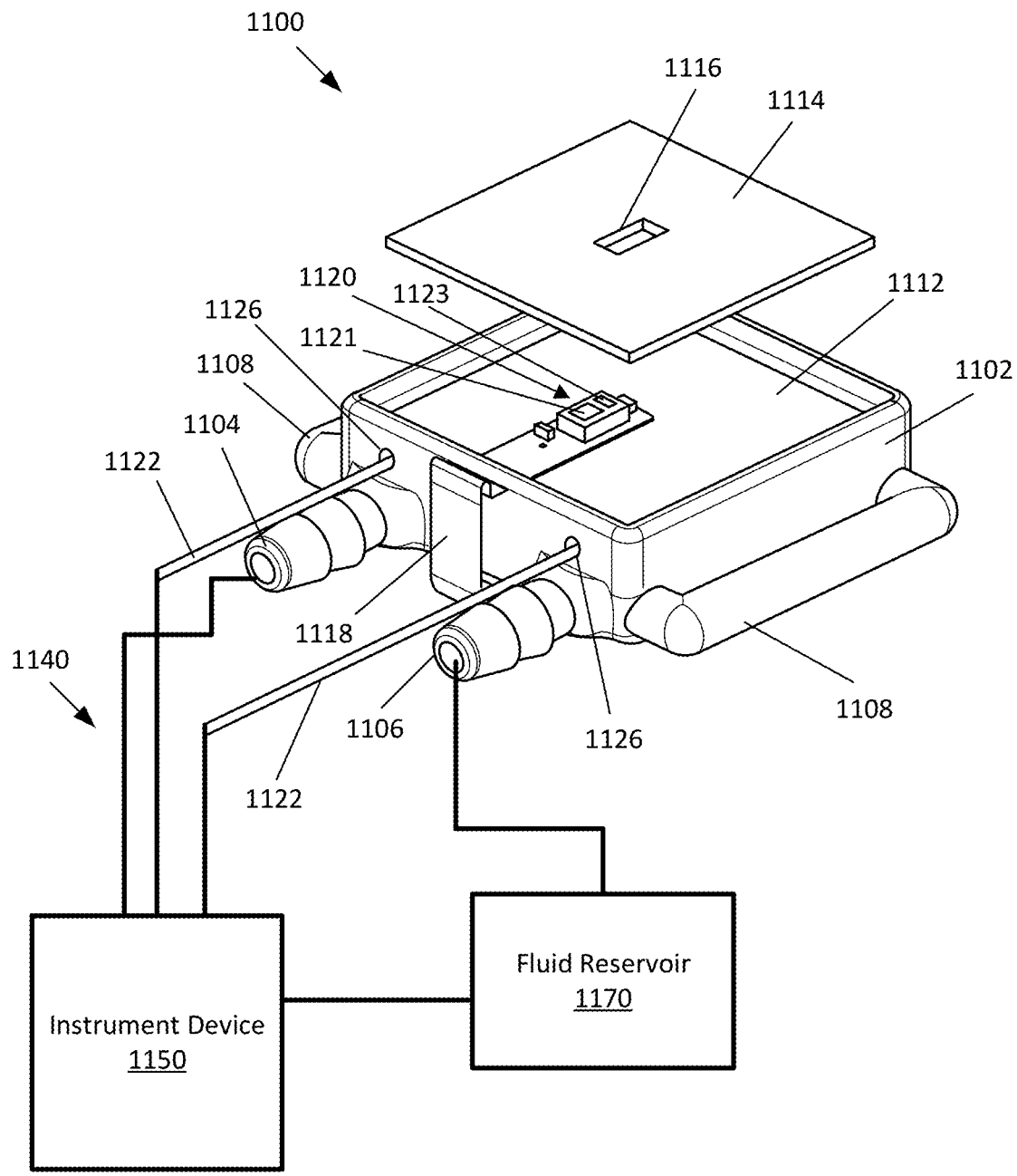
FIG. 23 is a perspective view of a sensor device according to another embodiment of the present disclosure.

FIG. 23 is a perspective view of a sensor device 1100 that detects a microvascular response for sepsis screening. The sensor device 1100 can share components with the sensor device 1002 described above with regard to FIGS. 9-20. The sensor device 1100 both induces and detects a microvascular response from a patient that can be compared to a normal response for determining whether the patient is likely to have sepsis. For example, the microvascular response can be induced by a rapid change in temperature, and variables such as a PPG waveform or an impedance waveform (see FIGS. 15 and 20) can be detected. The measured variables are compared before and after the temperature change. A non-septic response will exhibit a significant difference in the measured variables before and after the change in temperature, whereas a septic response will have a small or negligible difference.

The sensor device 1100 uses a coolant loop 1140 that is controlled by an instrument device 1150 to draw heat away from a heat pump 1112 and a sensor unit 1120 and toward a fluid reservoir 1170. The size of the fluid reservoir 1170, the capacity of the heat pump 1112, and the fluid flow rate generated by the instrument device 1150 are optimized to increase the rate of temperature change, while also improving the repeatability of the temperature change.

Advantageously, the controlled coolant loop 1140 decreases the mass of the sensor device 1100 because it replaces a dedicated heatsink on the sensor device such as the heatsink 1014 described above with respect to the sensor device 1002 of FIG. 10. Instead of a dedicated heatsink on the sensor device, the transfer of heat from the heat pump 1112 to the ambient air occurs at the fluid reservoir 1170 which is located separately from the sensor device 1100. Reducing the weight of the sensor device 1100 improves the accuracy and reliability of the sensor device 1100 because microvascular response signals can be distorted due to the pressure and forces applied to the blood vessels of the patient from the weight of the sensor device.

Additionally, the controlled coolant loop 1140 decreases the thermal inertia of the sensor device 1100 by reducing the amount of residual heat on the heat pump 1112 such that the sensor device is able to increase the rate of temperature change. For example, instead of the residual heat being dissipated by a dedicated heat sink located on the sensor device, the controlled coolant loop 1140 transfers the residual heat away from the sensor device 1100 and to the fluid reservoir 1170 which is located separately from the sensor device. Also, the coolant loop 1140 decreases the effect of room temperature on the performance of the sensor device 1100, and can improve the reliability of the sensor device 1100. By decreasing the effects of residual heat and room temperature, the rate of temperature change induced by the heat pump 1112 can increase which increases the detectability of the microvascular responses.

The heat pump 1112 is a solid-state thermoelectric heat pump that consumes electrical energy to transfer heat from one side surface to an opposite side surface of the heat pump 1112. The heat pump 1112 uses a Peltier effect to transfer heat from one side to the other such that the heat pump 1112 is a Peltier device. Depending on the direction of an electrical current, the heat pump 1112 either cools or heats the plate 1114.

A first side surface of the heat pump 1112 is thermally coupled to a plate 1114. A second side surface of the heat pump 1112 is thermally coupled to a fluid channel 1125 in which fluid from the coolant loop 1140 flows inside a housing 1102 of the sensor device 1110.

One or more cables 1122 supply control voltages to the heat pump 1112. The cables 1122 enter the housing 1102 of the sensor device 1100 through inlets 1126. In some embodiments, the cables 1122 supply about 9 amps of DC current to the heat pump 1112 such that the heat pump 1112 cools on one side surface and heats on an opposite side surface.

The plate 1114 is made from a solid material that contacts a skin surface of a patient when the sensor device 1100 is worn by the patient. In one embodiment, the plate 1114 is made from aluminum or a similar type of metal material. The plate 1114 includes an aperture 1116 to allow the sensor unit 1120 to have direct access to the skin surface of the patient when the sensor device 1100 is worn by the patient. As described above, the plate 1114 is thermally coupled to the heat pump 1112 such that the plate 1114 is cooled or heated by the heat pump 1112.

In some examples, the heat pump 1112 cools the plate 1114 to induce a temperature of about 18° C. on the skin surface of the patient. In some further examples, the heat pump 1112 heats the plate 1114 to induce a temperature of about 40° C. on the skin surface of the patient.

The sensor unit 1120 is mounted to a flexible cable 1118 that can bend around and conform to the shape of the housing 1102. The flexible cable 1118 is connected to one or more wires 1124 carried by a conduit 1142 (see FIGS. 26 and 27). The wires 1124 carry electrical power from a power supply 1158 (see FIG. 25) in the instrument device 1150 to the sensor unit 1120. The instrument device 1150 and power supply 1158 are located externally from the sensor device 1100 which advantageously reduces the weight of the sensor device 1100.

The sensor unit 1120 includes both an optical component 1121 and a thermal component 1123. The optical component 1121 is configured to measure vascular endothelial response. In one embodiment, the optical component 1121 is a PPG sensor similar to the PPG sensor 1004 described above with references to FIGS. 11-15.

The thermal component 1123 measures skin surface temperatures of the patient to provide a closed loop feedback control to ensure that the optical component 1121 measures the vascular endothelial response only at appropriate skin surface temperatures. For example, the closed loop feedback control ensures that the vascular endothelial responses are measured only when the skin surface has reached a certain predefined temperature (e.g., 18° C. or 40° C.) as a result of the temperature change that is induced by the plate 1114 of the sensor device 1100.

Figure 24:
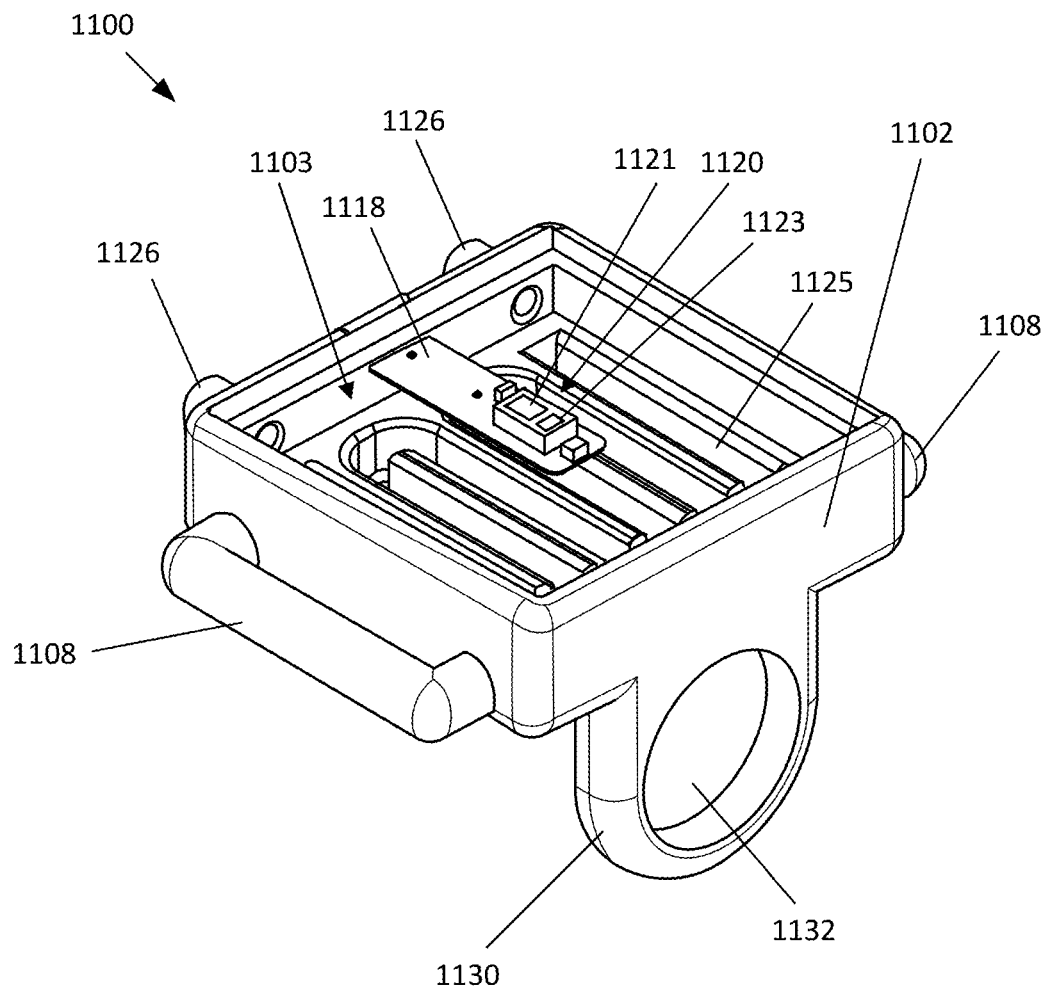
FIG. 24 illustrates a perspective view of a housing of the sensor device of FIG. 23.

FIG. 24 illustrates a perspective view of a housing 1102 of the sensor device 1100 with the heat pump 1112 removed therefrom. Referring now to FIGS. 23 and 24, the housing 1102 defines a cavity 1103 into which the heat pump 1112 is mounted inside. The housing 1102 is made from a durable plastic material. While the housing 1102 is illustrated in the figures as having a rectangular shaped body, a plurality of shapes and sizes are possible.

The housing 1102 defines an inlet 1104 where fluid pumped from the instrument device 1150 enters the fluid channel 1125 defined inside the housing 1102. The fluid pumped from the instrument device 1150 flows through the fluid channel 1125, and exits the housing 1102 through an outlet 1106 to return to the fluid reservoir 1170. The heat pump 1112 is mounted over the fluid channel 1125 and seals the fluid inside the fluid channel 1125 between the inlet 1104 and the outlet 1106. The fluid channel 1125 is shaped to have a serpentine configuration to increase the surface area contact between the fluid and the heat pump 1112.

One or more tabs 1108 are positioned on an exterior of the housing 1102. The tabs 1108 are structured to receive a strap or band that can be wrapped around a body part of a patient to attach the sensor device 1100 to the patient. In one embodiment, a strap or band is fastened to the tabs 1108 and is used to attach the sensor device 1100 to the wrist of a patient.

Additionally, a structure 1130 extends from the exterior of the housing 1102. The structure defines a loop 1132 that is structured to fix the conduit 1142 (see FIGS. 26 and 27) relative to the housing 1102. As will be described in more detail below, the conduit 1142 carries fluid to and away from the sensor device 1110, and also supplies electrical power to the sensor device 1110 to power the heat pump 1112 and the sensor unit 1120.

Figure 25:
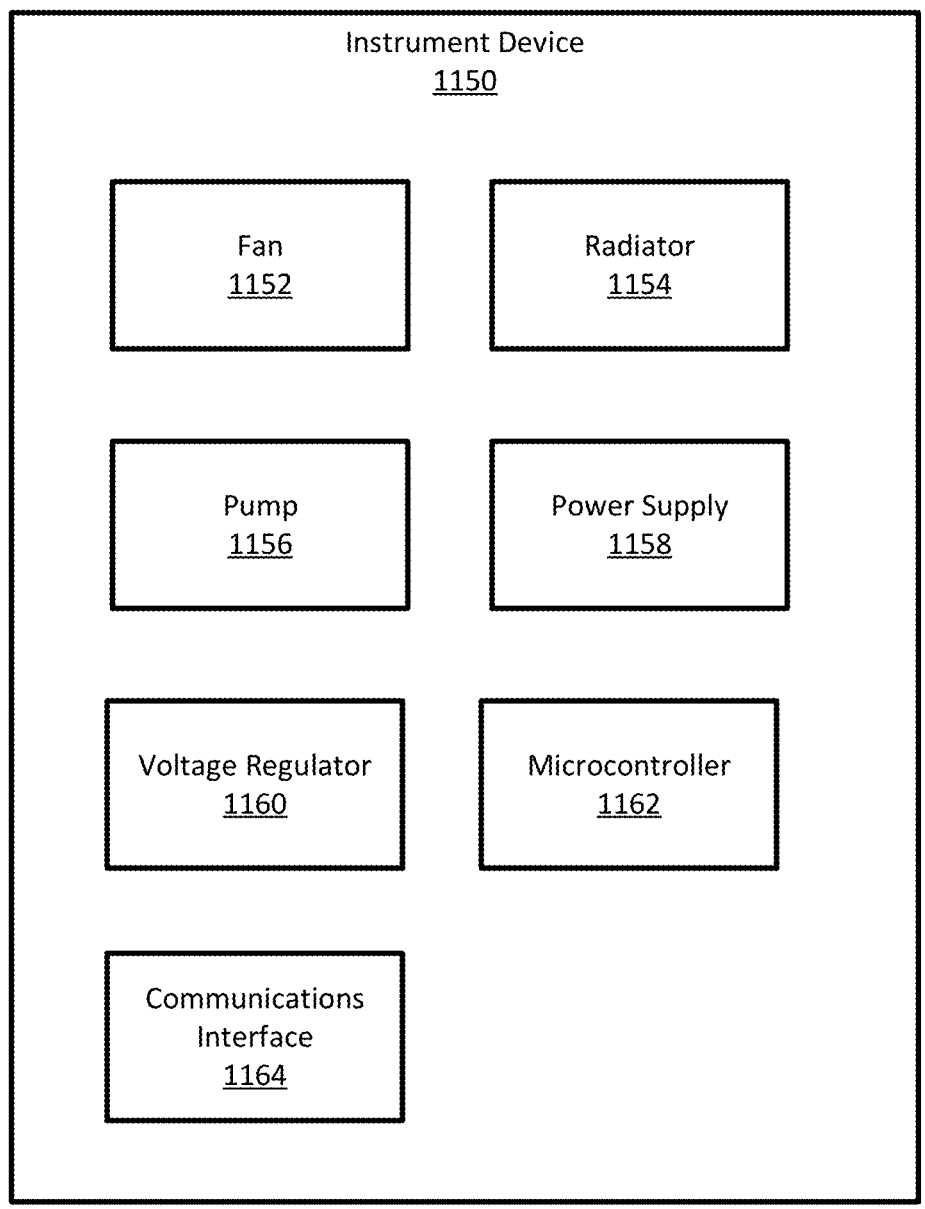
FIG. 25 schematically illustrates an instrument device that is structured to connect to the sensor device of FIG. 23.

FIG. 25 schematically illustrates the instrument device 1150. The instrument device 1150 includes a fan 1152, a radiator 1154, a pump 1156, a power supply 1158, a voltage regulator 1160, a microcontroller 1162, and a communications interface 1164. Additionally, while the fluid reservoir 1170 is illustrated in FIG. 23 as separate from the instrument device 1150, in some embodiments the instrument device 1150 includes the fluid reservoir 1170.

Referring now to FIGS. 23-25, the fan 1152 and radiator 1154 are used by the instrument device 1150 to cool the fluid held inside the fluid reservoir 1170. The pump 1156 is used by the instrument device 1150 to pump the cooled fluid from the fluid reservoir to the housing 1102 of the sensor device 1100. The fluid that is pumped from the fluid reservoir 1170 to the sensor device 1100 can be water or any other suitable type of fluid coolant.

The microcontroller 1162 is operably connected to the fan 1152, radiator 1154, pump 1156, power supply 1158, and voltage regulator 1160. The microcontroller 1162 can store one or more algorithms that utilize the voltage regulator 1160 to supply control voltages from the power supply 1158 to the heat pump 1112 to control the operation of the heat pump 1112. The power supply 1158 can also supply electrical power to the sensor unit 120. The microcontroller 1162 can be similar to the microcontroller 1024 described above.

The communications interface 1164 connects the instrument device 1150 to one or more external computing devices such as the computing device 1800 described above. Furthermore, the communications interface 1164 can be used to connect the instrument device 1150 to one or more display screens to display the vascular endothelial response data obtained from the sensor unit 1120 during operation of the sensor device 1100.

Figure 26:
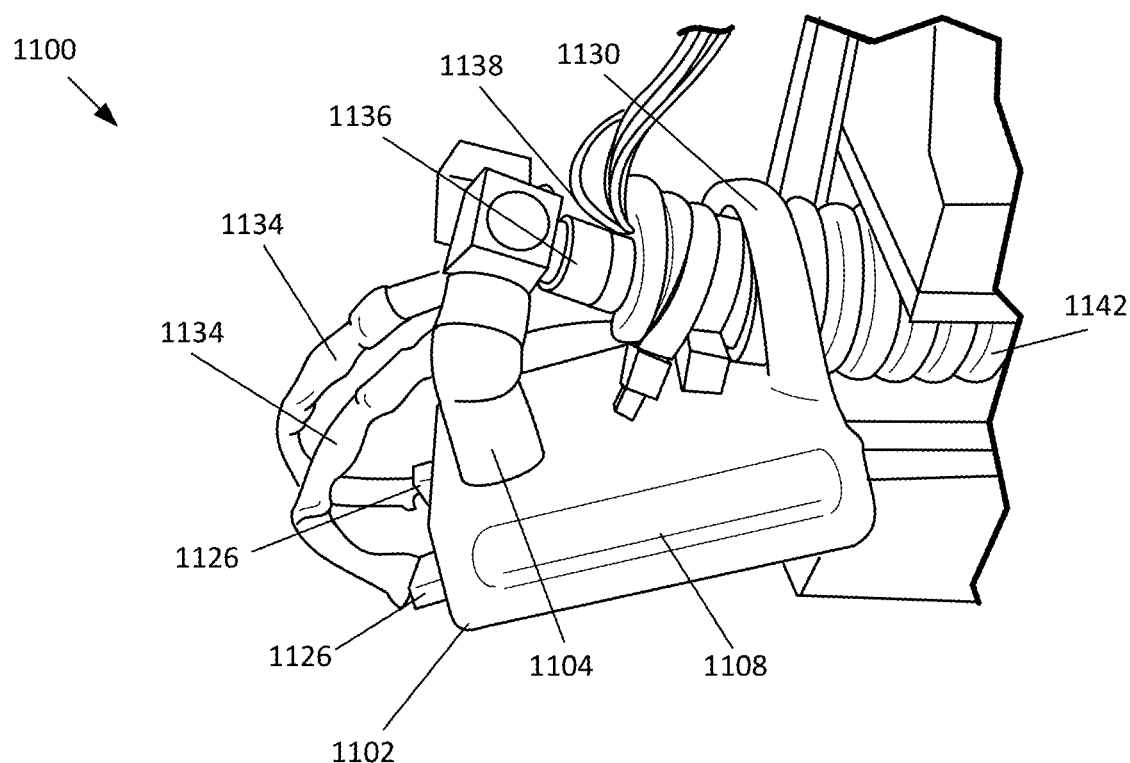
FIG. 26 illustrates a perspective view of the sensor device of FIG. 23 with a conduit tube extending therefrom.
Figure 27:
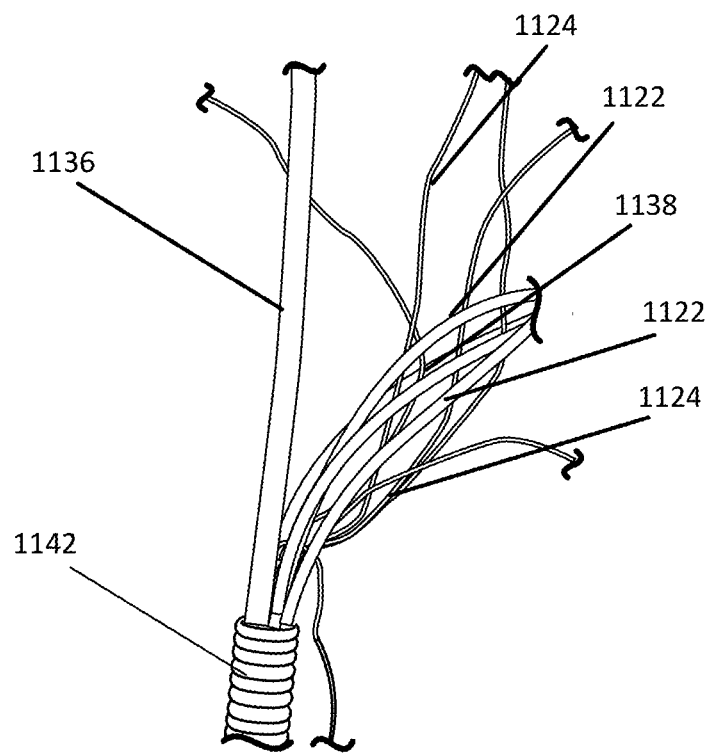
FIG. 27 illustrates internal components of the conduit tube of FIG. 26.

FIG. 26 illustrates a perspective view of the sensor device 1100 with the conduit 1142 extending therefrom. FIG. 27 illustrates the internal components of the conduit 1142. Referring now to FIGS. 26 and 27, the conduit 1142 connects the sensor device 1100 and instrument device 1150. The conduit includes an inlet tube 1136 to supply fluid from the fluid reservoir 1170 to the inlet 1104 of the sensor device 1100, and an outlet tube 1138 that transfers fluid from the outlet 1106 of the sensor device 1100 to the fluid reservoir 1170.

The conduit 1142 further includes one or more cables 1122 to supply control voltages from the power supply 1158 in the instrument device 1150 to the heat pump 1112. Additionally, in some embodiments, the conduit 1142 carries the one or more wires 1124 that carry electrical power from the power supply 1158 to the sensor unit 1120. In some further embodiments, the wires 1124 provide data communication between the sensor unit 1120 and the instrument device 1150. In some further embodiments, the sensor unit 1120 can wirelessly communicate with the instrument device 1150 and one or more additional devices using a network such as the networks 210, 2210 described above with reference to FIGS. 2 and 21.

Figure 28:
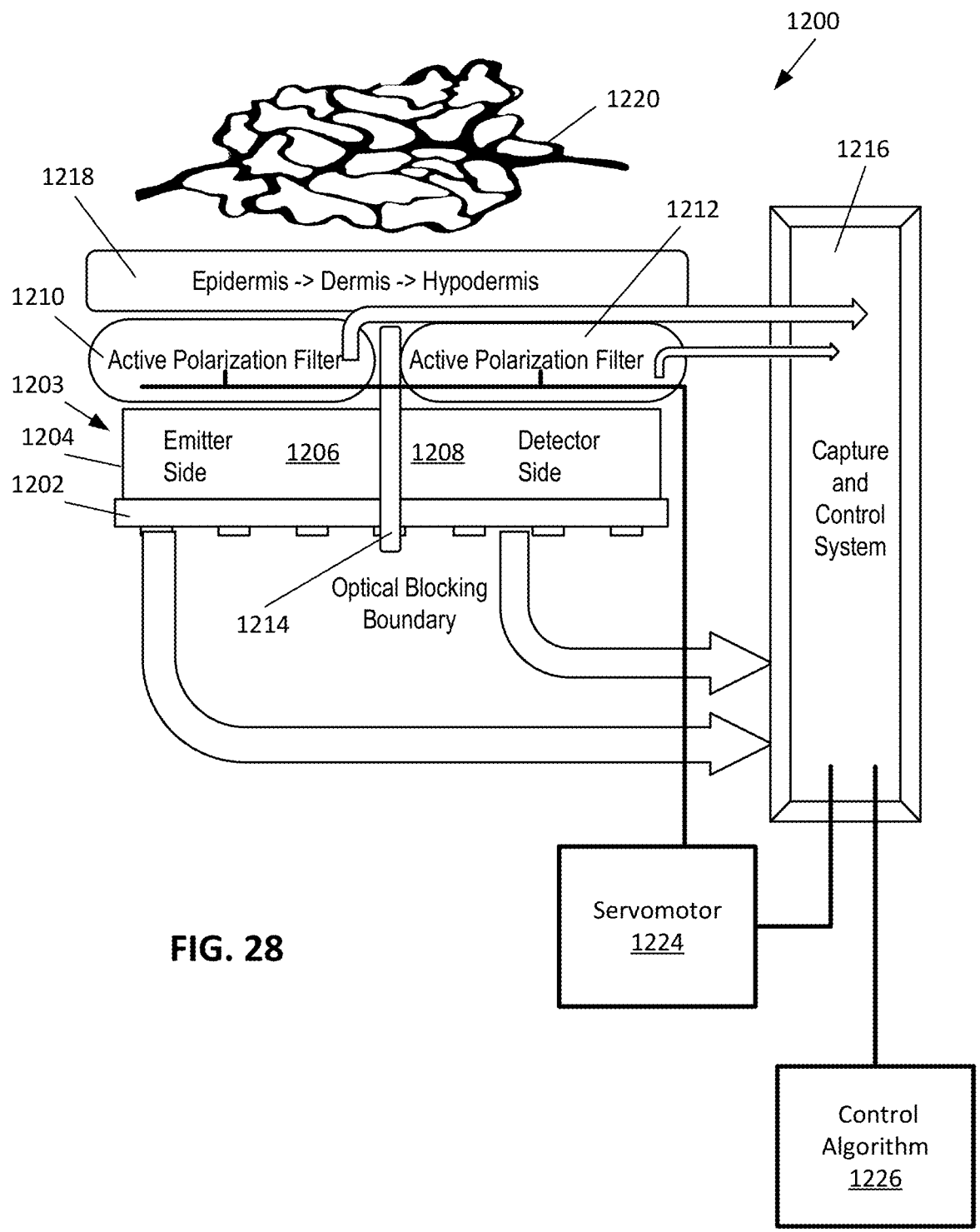
FIG. 28 schematically illustrates a sensor device according to another embodiment of the present disclosure.

FIG. 28 schematically illustrates a sensor device 1200 in accordance with another example embodiment of the present disclosure. While the following description is directed to the sensor device 1200, it is noted that the features described with respect to the sensor device 1200 can also be applied to the sensor devices 1002, 1100 described above. Similarly, the features described above with respect to the sensor devices 1002, 1100 can also be applied to the sensor device 1200. For example, the sensor device 1200 can include the heat pump 1112 and plate 1114, as well as the housing 1102 and fluid channel 1125 of the sensor device 1100, as well as additional features of the sensor devices 1002, 1100 described above.

Referring now to FIG. 28, the sensor device 1200 includes an optical component 1203. In some embodiments, the optical component 1203 of the sensor device 1200 can be used as the optical component 1004, 1006, 1121 of the sensor devices 1002, 1100.

The optical component 1203 has a body 1204 that is mounted to a substrate 1202. In some embodiments, the substrate 1202 is an electrical circuit board. The optical component 1203 further includes a light emitter 1206 to transmit optical signals that penetrate a skin surface 1218 to reach a blood vessel 1220, a light detector 1208 to receive optical signals reflected back from the blood vessel 1220, and first and second polarizers 1210, 1212 that filter the optical signals.

Figure 29:
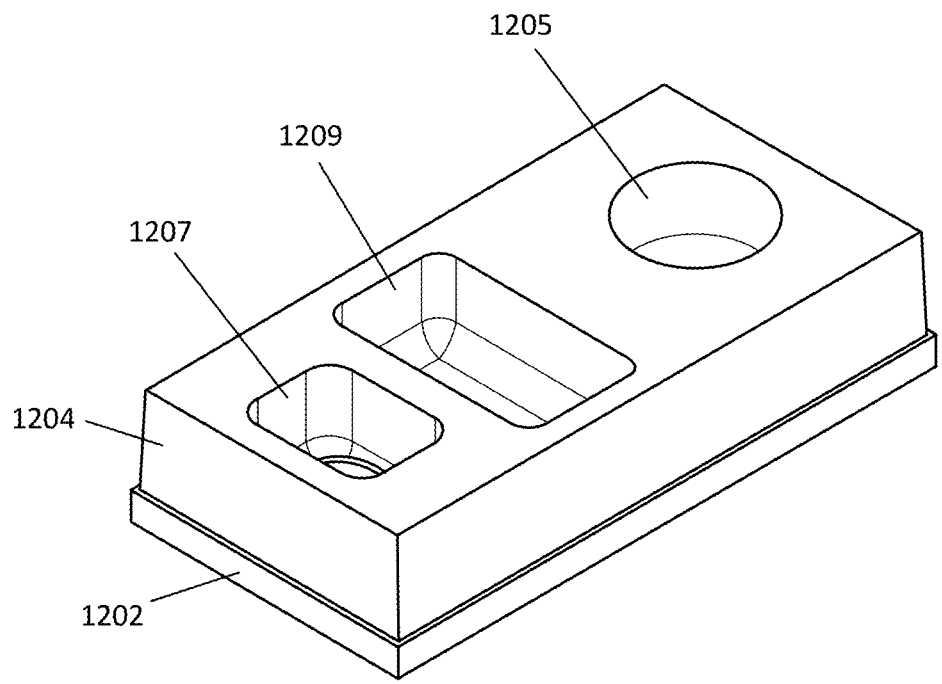
FIG. 29 illustrates a perspective view of a housing of the sensor device of FIG. 28.

FIG. 29 illustrates a perspective view of the body 1204 of the optical component 1203. Referring now to FIGS. 28 and 29, the body 1204 defines a first lateral cavity 1205 that houses the light emitter 1206 and a second lateral cavity 1207 that houses the light detector 1208. The body 1204 further defines a central cavity 1209 that is positioned between the first and second lateral cavities 1205, 1207. The central cavity 1209 houses an optical block 1214.

The light emitter 1206 is configured to project light signals onto the skin surface 1218 such that the light signals penetrate the skin surface 1218 and reach a blood vessel 1220 before being scattered and reflected back to the light detector 1208. The light emitter 1206 can include one or more light-emitting diodes (LEDs). In some embodiments, the light emitter 1206 emits the optical signals in the form of infrared (IR) and visible red light.

The light detector 1208 is configured to receive the light signals that are scattered and reflected back from the blood vessel 1220. The light detector 1208 measure changes in the infra-red (IR) and red light absorption in the blood vessel 1220. In some embodiments, the light detector 1208 includes one or more photodetectors or photodiodes.

The optical block 1214 is configured to prevent the light signals that are projected from the light emitter 1206 from passing directly to the light detector 1208 (i.e., without first being reflected back from the blood vessel 1220), and similarly blocks the light scattered and reflected back from the blood vessel 1220 from reaching the light emitter 1206.

The first polarizer 1210 is mounted over the light emitter 1206. The first polarizer 1210 polarizes the light signals from the light emitter 1206 in a polarized direction.

The second polarizer 1212 is mounted over the light detector 1208. The second polarizer 1212 is arranged to be out of phase with respect to the first polarizer 1210. The second polarizer 1212 acts as an optical filter to reduce and/or eliminate noise in the reflected optical signals received by the light detector 1208. More specifically, the second polarizer 1212 filters the reflected optical signals so that only the optical signals that reflect off the blood vessel 1220 are received by the light detector 1208, while the optical signals that reflect off of the skin surface 1218, and that accordingly do not reach the blood vessel 1220, are blocked.

The first and second polarizers 1210, 1212 operate to filter the reflected optical signals as follows. The optical signals reflected from the skin surface 1218 remain polarized in the direction defined by the first polarizer 1210. Since the second polarizer 1212 is out of phase with respect to the first polarizer 1210, the optical signals reflected from the skin surface 1218 are blocked from reaching the light detector 1208. In contrast, the optical signals that reflect off of the blood vessel 1220 are no longer polarized such that these optical signals are able to pass through the second polarizer 1212 and reach the light detector 1208. In this manner, the glare from the skin surface 1218 is blocked from reaching the light detector 1208, and only the optical signals that reflect off of the blood vessel 1220 are received by the light detector 1208.

The first and second polarizers 1210, 1212 can be linear, elliptical, or circular polarizers. As an illustrative example, the first and second polarizers 1210, 1212 can be arranged on the optical component 1203 to be 90 degrees out of phase with respect to one another.

Additionally, the first and second polarizers 1210, 1212 are independently adjustable on the optical component 1203 such that the angle of incidence or reflection of each of the first and second polarizers 1210, 1212 is adjustable. Advantageously, the orientation of the first and second polarizers 1210, 1212 can be adjusted to align with the orientation of the blood vessel 1220 to maximize the strength of the optical signals reflected back from the blood vessel 1220 regardless of the position of the sensor device 1200 with respect to the blood vessel 1220. For example, the blood vessel 1220 has endothelial cells that are aligned in a particular orientation such that when the polarized light from the light emitter 1206 is aligned with orientation of the endothelial cells, the reflected light signals from the blood vessel will be maximal.

A capture and control system 1216 controls the operation of the optical component 1203 including the transmission of light signals from light emitter 1206 and the capture of data from the reflected light signals received by the light detector 1208.

Additionally, the capture and control system 1216 controls the phase angle of the first and second polarizers 1210, 1212. In one embodiment, the capture and control system 1216 uses the data from the reflected light signals received by the light detector 1208 to determine an orientation of the blood vessel 1220, and to adjust the phase angle of the polarizers.

The phase angles of the first and second polarizers 1210, 1212 are also modulated based on the induced temperature that results from the heat pump 1112 by using a temperature look up table that correlates a desired phase angle based on the induced temperature. As an illustrative example, for a given induced temperature (e.g., 50° Fahrenheit), the phase angle of the first polarizer 1210 may lead the phase angle of the second polarizer 1212, whereas for another given induced temperature (e.g., 120° Fahrenheit), the phase angle of the first polarizer 1210 may lag the phase angle of the second polarizer 1212. Accordingly, the relative polarization phase angles (i.e., polarization set points) of the first and second polarizers 1210, 1212 may vary based on the induced temperature change that results from the operation of the heat pump.

In one embodiment, the capture and control system 1216 controls one or more servomotors 1224 operably connected to the first and second polarizers 1210, 1212 to mechanically adjust the phase angles of the polarizers. Additional means can be used to adjust the phase angles of the first and second polarizers 1210, 1212.

Additionally, the capture and control system 1216 stores a control algorithm 1226 for calibration of the sensor device 1200 to optimally detect a vascular endothelial response. While the control algorithm 1226 is described with reference to the sensor device 1200, the control algorithm 1226 can also be performed by the sensor devices 1002, 1100 described above.

Figure 30:
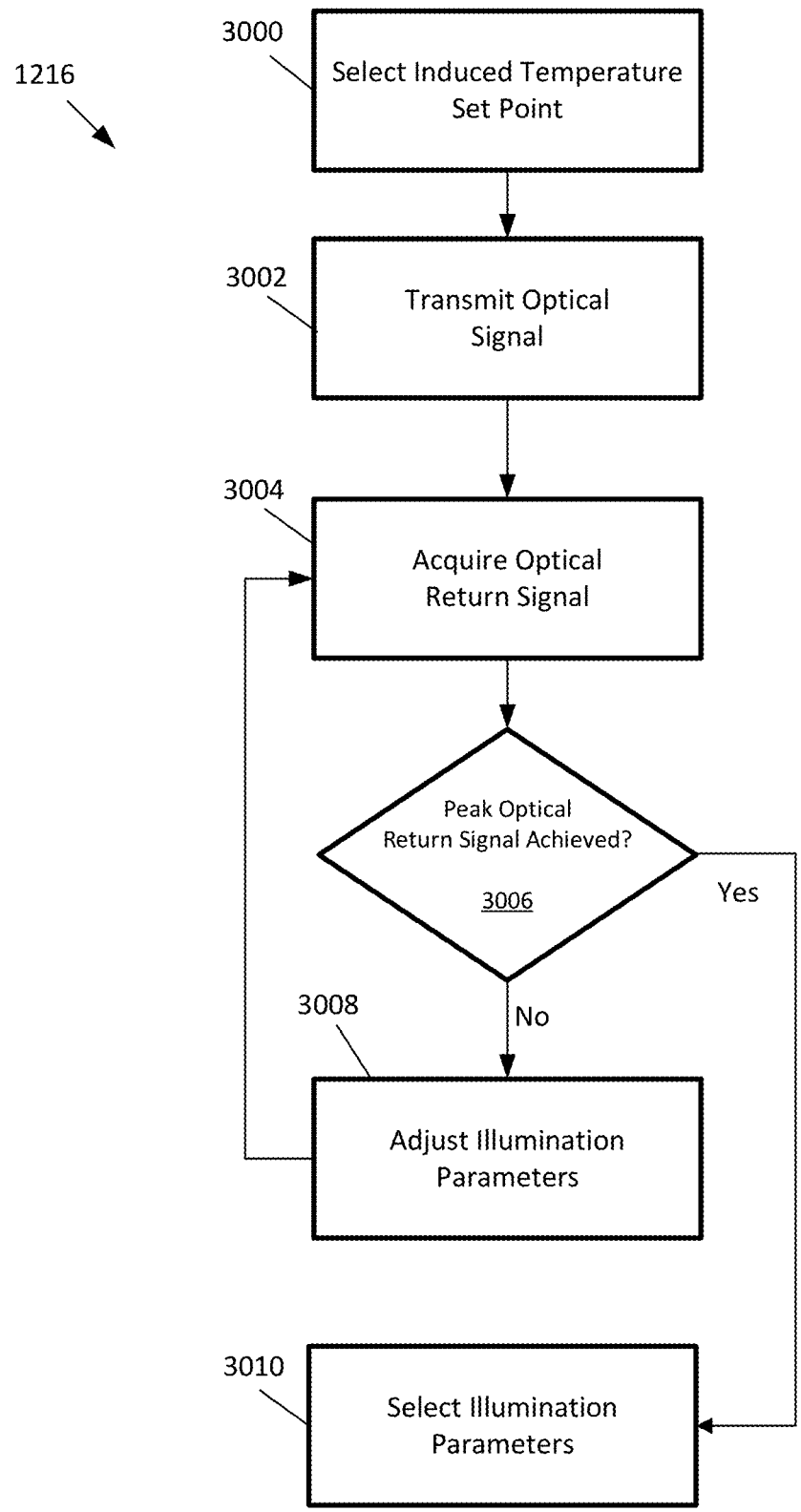
FIG. 30 illustrates a control algorithm for the sensor device of FIG. 28.

FIG. 30 illustrates the operations of the control algorithm 1226. The control algorithm 1226 modulates the illumination channels of the light emitter 1206 with respect to the induced temperature changes from the heat pump and desired vascular endothelial response parameters.

Referring now to FIG. 30, the control algorithm 1226 includes an operation 3000 of selecting an induced temperature set point generated by a heat pump (e.g., such as the heat pump 1112 described above). Next, the control algorithm 1226 includes an operation 3002 of transmitting an optical signal to the blood vessel 1220 by using the light emitter 1206 followed by an operation 3004 of acquiring an optical return signal from the light detector 1208.

Next the control algorithm 1226 includes an operation 3006 of determining whether a peak optical return signal is acquired. When a peak optical return signal is not acquired (i.e., "No" at operation 3006), the control algorithm 1226 proceeds to operation 3008 to adjust one or more illumination parameters of the light emitter 1206 and then proceeds to repeat operations 3002-3006. When a peak optical return signal is acquired (i.e., "Yes" at operation 3004), the control algorithm 1226 proceeds to operation 3010 of selecting the illumination parameters as optimal for the induced temperature set point. Thereafter, the control algorithm 1226 can be repeated for additional induced temperature set points.

At operation 3008, the amount of light can be modulated, the pulse length of the light (duration of the light pulses longer vs. shorter) can be modulated, the illumination voltages can be modulated, and the like. Additionally, the control algorithm 1226 can be used to determine the adjustment of the first and second polarizers 1210, 1212 based on the optical return signal.

The block diagrams depicted herein are just examples. There may be many variations to these diagrams described therein without departing from the spirit of the disclosure. For instance, components may be added, deleted or modified.

While embodiments have been described, it will be understood that those skilled in the art, both now and in the future, may make various improvements and enhancements.

As used herein, "about" refers to a degree of deviation based on experimental error typical for the particular property identified. The latitude provided the term "about" will depend on the specific context and particular property and can be readily discerned by those skilled in the art. The term "about" is not intended to either expand or limit the degree of equivalents which may otherwise be afforded a particular value. Further, unless otherwise stated, the term "about" shall expressly include "exactly," consistent with the discussions regarding ranges and numerical data. Concentrations, amounts, and other numerical data may be expressed or presented herein in a range format. It is to be understood that such a range format is used merely for convenience and brevity and thus should be interpreted flexibly to include not only the numerical values explicitly recited as the limits of the range, but also to include all the individual numerical values or sub-ranges encompassed within that range as if each numerical value and sub-range is explicitly recited. As an illustration, a numerical range of "about 4 percent to about 7 percent" should be interpreted to include not only the explicitly recited values of about 4 percent to about 7 percent, but also include individual values and sub-ranges within the indicated range. Thus, included in this numerical range are individual values such as 4.5, 5.25 and 6 and sub-ranges such as from 4-5, from 5-7, and from 5.5-6.5; etc. This same principle applies to ranges reciting only one numerical value. Furthermore, such an interpretation should apply regardless of the breadth of the range or the characteristics being described.

The description and illustration of one or more embodiments provided in this application are not intended to limit or restrict the scope of the invention as claimed in any way. The embodiments, examples, and details provided in this application are considered sufficient to convey possession and enable others to make and use the best mode of claimed invention. The claimed invention should not be construed as being limited to any embodiment, example, or detail provided in this application. Regardless whether shown and described in combination or separately, the various features (both structural and methodological) are intended to be selectively included or omitted to produce an embodiment with a particular set of features. Having been provided with the description and illustration of the present application, one skilled in the art may envision variations, modifications, and alternate embodiments falling within the spirit of the broader aspects of the claimed invention and the general inventive concept embodied in this application that do not depart from the broader scope.

What is claimed is:

1. A system for evaluating a septic patient, the system comprising:
   a patient support device including a frame connected to a motor, the frame configured to tilt from a rested position to a tilted position;
   a sensor configured to non-invasively measure one or more vital signs before and after the frame is tilted; and
   a control device having a processor and a memory, wherein the memory stores instructions that, when executed by the processor, cause the control device to:
      obtain a first vital sign measurement from the septic patient when the frame is in the rested position;
      tilt the frame from the rested position into the tilted position;
      obtain a second vital sign measurement from the septic patient when the frame is in the tilted position; and
      determine whether a status of the septic patient is improving based on the first and second vital sign measurements.

2. The system of claim 1, wherein the patient support device is a hospital bed.

3. The system of claim 1, wherein the frame includes an upper portion and a lower portion, and the tilted position includes tilting the lower portion to raise a leg of the septic patient causing blood to flow from the leg toward the septic patient's heart.

4. The system of claim 1, wherein the instructions, when executed by the processor, further cause the control device to:
   compare the second vital sign measurement to the first vital sign measurement to determine a macrovascular response.

5. The system of claim 4, wherein the instructions, when executed by the processor, further cause the control device to:
   determine whether the septic patient is responding to fluid resuscitation treatment based on the macrovascular response.

6. The system of claim 5, wherein the instructions, when executed by the processor, further cause the control device to:
   terminate the fluid resuscitation treatment when it is determined that the septic patient is not responding to the fluid resuscitation treatment.

7. The system of claim 5, wherein the instructions, when executed by the processor, further cause the control device to:
   continue the fluid resuscitation treatment when it is determined that the septic patient is responding to the fluid resuscitation treatment.

8. The system of claim 1, wherein the instructions, when executed by the processor, further cause the control device to:
   control the frame to tilt at predetermined intervals; and
   control the sensor to automatically obtain vital sign measurements from the septic patient before and after each predetermined interval.

9. The system of claim 8, wherein the instructions, when executed by the processor, further cause the control device to:
   trend the vital sign measurements over time to determine a macrovascular response; and
   determine whether the septic patient is responding to fluid resuscitation treatment based on the macrovascular response.

10. The system of claim 1, wherein the first and second vital sign measurements include at least one of heart rate, stroke volume, cardiac output, blood pressure, and mean arterial pressure.

11. A method of evaluating a septic patient, the method comprising:
    positioning a patient support device into a rested position, the patient support device supporting the septic patient;
    obtaining a first vital sign measurement from the septic patient when the patient support device is in the rested position;
    tilting the patient support device from the rested position into a tilted position;
    obtaining a second vital sign measurement from the septic patient when the patient support device is in the tilted position; and
    determining whether a status of the septic patient is improving based on the first and second vital sign measurements.

12. The method of claim 11, further comprising:
    tilting a lower portion of the patient support device to raise a leg of the septic patient causing blood to flow from the leg toward the septic patient's heart.

13. The method of claim 11, further comprising:
    comparing the second vital sign measurement to the first vital sign measurement to determine a macrovascular response.

14. The method of claim 13, further comprising:
    determining whether the septic patient is responding to fluid resuscitation treatment based on the macrovascular response.

15. The method of claim 14, further comprising:
    terminating the fluid resuscitation treatment when it is determined that the septic patient is not responding to the fluid resuscitation treatment.

16. The method of claim 14, further comprising:
    continuing the fluid resuscitation treatment when it is determined that the septic patient is responding to the fluid resuscitation treatment.

17. The method of claim 11, wherein the first and second vital sign measurements include at least one of heart rate, stroke volume, cardiac output, blood pressure, and mean arterial pressure.

18. The method of claim 11, further comprising:
    positioning the patient support device to tilt at predetermined intervals; and
    obtaining vital sign measurements from the septic patient before and after each predetermined interval.

19. The method of claim 18, further comprising:
    trending the vital sign measurements over time to determine a macrovascular response; and
    determining whether the septic patient is responding to fluid resuscitation treatment based on the macrovascular response.

20. A system for evaluating a septic patient, the system comprising:
    at least one processing device; and
    a memory, wherein the memory stores instructions that, when executed by the at least one processing device, cause the at least one processing device to:
       position a patient support device into a rested position, the patient support device supporting the septic patient;
       obtain a first vital sign measurement from the septic patient when the patient support device is in the rested position;

tilt the patient support device from the rested position into a tilted position;
obtain a second vital sign measurement from the septic patient when the patient support device is in the tilted position; and
determine whether a status of the septic patient is improving based on the first and second vital sign measurements.

* * * * *